(12) United States Patent
Light

(10) Patent No.: US 10,350,246 B2
(45) Date of Patent: Jul. 16, 2019

(54) BIOENGINEERED ADIPOCYTES FOR THE LIGHT-CONTROLLED RELEASE OF INSULIN AND OTHER PEPTIDES

(71) Applicant: THE GOVERNORS OF THE UNIVERSITY OF ALBERTA, Edmonton (CA)

(72) Inventor: Peter Edward Light, Sherwood Park (CA)

(73) Assignee: THE GOVERNORS OF THE UNIVERSITY OF ALBERTA, Edmondton (CA)

( * ) Notice: Subject to any disclaimer, the term of this patent is extended or adjusted under 35 U.S.C. 154(b) by 0 days.

(21) Appl. No.: 15/524,784

(22) PCT Filed: Nov. 6, 2015

(86) PCT No.: PCT/CA2015/051150
§ 371 (c)(1),
(2) Date: May 5, 2017

(87) PCT Pub. No.: WO2016/070286
PCT Pub. Date: May 12, 2016

(65) Prior Publication Data
US 2017/0333486 A1 Nov. 23, 2017

Related U.S. Application Data

(60) Provisional application No. 62/076,599, filed on Nov. 7, 2014.

(51) Int. Cl.
| | |
|---|---|
| *A01N 63/00* | (2006.01) |
| *C12N 15/63* | (2006.01) |
| *C07H 21/04* | (2006.01) |
| *A61K 35/35* | (2015.01) |
| *A61K 41/00* | (2006.01) |
| *C07K 14/575* | (2006.01) |
| *C07K 14/62* | (2006.01) |
| *C07K 14/405* | (2006.01) |
| *C12N 5/077* | (2010.01) |
| *A61K 38/28* | (2006.01) |
| *C12N 15/86* | (2006.01) |
| *C12N 15/79* | (2006.01) |

(52) U.S. Cl.
CPC ............. *A61K 35/35* (2013.01); *A61K 38/28* (2013.01); *A61K 41/00* (2013.01); *C07K 14/405* (2013.01); *C07K 14/575* (2013.01); *C07K 14/62* (2013.01); *C12N 5/0653* (2013.01); *C07H 21/04* (2013.01); *C07K 2319/036* (2013.01); *C12N 15/79* (2013.01); *C12N 15/86* (2013.01); *C12N 2501/33* (2013.01); *C12N 2510/02* (2013.01)

(58) Field of Classification Search
CPC ........ A61K 35/35; C12N 15/79; C12N 15/86; C12N 2510/00; C07H 21/04
USPC ........... 424/93.21; 435/320.1; 536/23.5, 24.1
See application file for complete search history.

(56) References Cited

U.S. PATENT DOCUMENTS

2007/0261127 A1   11/2007  Boyden
2013/0274838 A1*  10/2013  Entcheva et al.

OTHER PUBLICATIONS

Wang et al., 2007, Molecular and Cellular Biology, vol. 27, No. 10, p. 3716-3731.*
Linscheid et al., 2003, Endocrinology, vol. 144, p. 5578-5584.*
Yizhar et al. (2011), Nature, vol. 477, pp. 171-178.
Zhang et al. (2008), Nature Neuroscience, vol. 11, No. 6, pp. 631-633.
Zhang et al. (2012), Journal of Cellular Physiology, vol. 227(5), pp. 1972-1979.
Zulewski et al. (2001), Diabetes, vol. 50(3), pp. 521-533.
PCT International Search Report and Written opinion in respect of PCT/CA2015/051150.
Reinbothe et al. (2014), Islets, vol. 6, pp. e-28095-1 to 8.
Chakrabarti (2010), Endocrinology, vol. 151(6), pp. 2408-2410.
Lee et al. (2013), Diabetes, vol. 62, pp. 864-874.
O'Neill et al. (2014), Gene Therapy, vol. 21, pp. 653-661.
Armentano et al. (1990), Procur. Natl. Acad. Sci. USA, vol. 87, pp. 6141-6145.
Assady et al. (2001), Diabetes, vol. 50, pp. 1691-1697.
Berkner et al. (1988). BioTechniques, vol. 6, No. 7, p. 616.
Berndt et al. (2009), Nature Neuroscience, vol. 12, No. 2, pp. 229-234.
Berndt et al. (2011), Proc. Natl. Acad. Sci. USA, vol. 108, No. 18, pp. 7595-7600.
Cammisotto PG & Bukowiecki LJ (2004), Am J Physiol Regul Integr Comp Physiol, vol. 287, pp. R1380-1386.
Chowdhury et al. (1991), Science, vol. 254, pp. 1802-1805.

(Continued)

Primary Examiner — Shin Lin Chen
(74) Attorney, Agent, or Firm — S. Serge Shahinian

(57) ABSTRACT

The present application discloses the use of light-gated cation-selective channelrhodopsins (Ch Rs) for the optogenetic control of the secretion of a polypeptide of interest in adipocytes. Engineered adipocytes comprising a channelrhodopsin (ChR) polypeptide, and/or a nucleic acid encoding same, and a secretory polypeptide precursor comprising a bioactive polypeptide and a signal peptide suitable for secretion of the bioactive polypeptide by the engineered adipocytes, and/or a nucleic acid encoding same, are disclosed. The use of such engineered adipocytes for the management or treatment of diseases/conditions in which the secretion of a polypeptide of interest is beneficial, such as the secretion of insulin in diabetic patients, is also disclosed.

15 Claims, 13 Drawing Sheets
Specification includes a Sequence Listing.

(56) References Cited

OTHER PUBLICATIONS

Dai et al. (1992), Proc. Natl. Acad. Sci. USA, vol. 89, pp. 10892-10895.
Danos and Mulligan (1988), Proc. Natl. Acad. Sci. USA, vol. 85, pp. 6460-6464.
Eglitis et al. (1985), Science, vol. 230, pp. 1395-1398.
Ferry et al. (1991), Proc. Natl. Acad. Sci. USA, vol. 88, pp. 8377-8381.
Flotte et al. (1992), American Journal of Respiratory Cell and Molecular Biology, vol. 7, pp. 349-356.
Flotte et al. (1993), The Journal of Biology Chemistry vol. 268, No. 5, pp. 3781-3790.
Fujimoto et al (2005), Molecular and Celular Biochemistry, vol. 268, pp. 1-8.
Gunaydin et al.(2010), Nature Neuroscience, vol. 13, No. 3, pp. 387-392.
Hermonat et al. (1984), Proc. Natl. Acad. Sci. USA, vol. 81, pp. 6466-6470.
Herz and Gerard (1993), Proc. Natl. Acad. Sci. USA, vol. 90, pp. 2812-2816.
Hochbaum et al. (2014), Nature Methods, vol. 11, No. 8, pp. 825-833.
Huber et al. (1991), Proc. Natl. Acad. Sci. USA, vol. 88, pp. 8039-8043.
Hwu et al. (1993), Journal of Immunology, vol. 150, No. 9, pp. 4104-4115.
Ito et al. (2005), Diabetologia, vol. 48, pp. 1614-1620.
Kay et al. (1992), Human Gene Therapy, vol. 3, pp. 641-647.
Klapoetke et al. (2014), Nathure Methods, vol. 11, No. 3, pp. 338-346.
Kleinlogel et al. (2011), Nature Neuroscience, vol. 14, No. 4, pp. 513-518.
Knopfel et al. (2010), The Journal of Neuroscience, vol. 30(45), pp. 14998-15004.
Lemarchand et al. (1992), Proc. Natl. Acad. Sci. USA, vol. 89, pp. 6482-6486.
Lin et al. (2009), Biophys Journal, vol. 96(5). pp. 1803-1814.
Lin et al. (2013), Nature Neuroscience, vol. 16, No. 10, pp. 1499-1508.
Lin, J.Y. (2010), Exp. Physiol,vol. 96.1, pp. 1499-1508.
McLaughlin et al. (1988), Journal of Virology, vol. 62, No. 6, pp. 1963-1973.
Miller, A.D. (1990), Blood, vol. 76, No. 2, pp. 271-278.
Muzyczka et al. (1992), Curent Topics in Mcrobiology and Immunology, vol. 158, pp. 97-129.
Nagel et al. (2005), Current Biology, vol. 15, pp. 2279-2284.
Nagel et al. (2003), Proc. Natl. Acad. Sci. USA, vol. 100, No. 24, pp. 13940-13945.
Oguri et al. (2010), Am J Physiol Cell Physiol, vol. 298, pp. C1414-C1423.
Quantin et al. (1992), Proc. Natl. Acad. Sci. USA, vol. 89, pp. 2581-2584.
Rosenfeld et al. (1991), Science, vol. 252, pp. 431-434.
Rosenfeld et al. (1992), Cell, vol. 68, pp. 143-155.
Roy et al. (2003), Endocrinology, vol. 144(4), pp. 1585-1593.
Samulski et al. (1989), The Journal of Virology, vol. 63, No. 9, pp. 3822-3828.
Tang et al. (2004), Diabetes, vol. 53(7), pp. 1721-1732.
Tratschin et al. (1984), Journal of Biology, vol. 51, No. 3, pp. 611-619.
Tratschin et al. (1985), Molecular and Cellular Biology, vol. 4, No. 10, pp. 2072-2081.
Tratschin et al. (1985), Molecular and Cellular Biology, vol. 5, No. 11, pp. 3251-3260.
Van Beusechem et al. (1992), Proc. Natl. Acad. Sci. USA, vol. 89, pp. 7640-7644.
Wang et al. (2010), Endocrinology, vol. 151(6), pp. 2933-2939.
Wen et al. (2010), PLoS One, vol. 5, No. 9, pp. 1-13.
Wilson et al. (1998), Proc. Natl. Acad. Sci. USA, vol. 85, pp. 3014-3018.
Wondisford et al. (1988), Molecular Endocrinology, vol. 2, No. 1, pp. 32-39.
Yang et al. (2002), Proc. Natl. Acad. Sci. USA, vol. 99, No. 12, pp. 8078-8080.

* cited by examiner

NotI  Kozak                    Leptin Signal Peptide (SEQ ID NO: 26)                    ][
gcggccgcGCCACCATGCATTGGGGAACCCTGTGCGGATTCTTGTGGCTTTGGCCCTATCTTTTCTATGTCCAAGCTTTTGTGAAC B-chain (SEQ ID NO: 27)                                          F       F
CAACACCTGTGCGGCTCACACCTGGTGAAGCTCTCTACCTAGTGTGCGGGAACGAGGCTTCTTCTACACACCCCGTACCAAGCG ][                              C-peptide (SEQ ID NO:28)
GGAGGCAGAGGACCTGCAGGTGGGGCAGGTGGAGCTGGGCGGGGGCCCTGGTGCAGGCAGCCTGCAGCCCTTGGCCCTGGAGGGGT F       ][                    A-chain (SEQ ID NO:29)                          ]
CCCGTCAGAAGCGTGGCATTGTGGAACAATGCTGTACCAGCATCTGCTCCCTCTACCAGCTGGAGAACTACTGCAACTAGcgtacg CCCCCCCCCCTAACGTTACTGGCCGAAGCCGCTTGGAATAAGGCCGGTGTGCGTTTGTCTATATGTTATTTTCCACCATATTGCCG
TCTTTTGGCAATGTGAGGGCCCGGAAACCTGGCCCTGTCTTCTTGACGAGCATTCCTAGGGGTCTTTCCCCTCTCGCCAAAGGAAT
GCAAGGTCTGTTGAATGTCGTGAAGGAAGCAGTTCCTCTGGAAGCTTCTTGAAGACAAACAACGTCTGTAGCGACCCTTTGCAGGC
AGCGGAACCCCCCACCTGGCGACAGGTGCCTCTGCGGCCAAAAGCCACGTGTATAAGATACACCTGCAAAGGCGGCACAACCCCAG
TGCCACGTTGTGAGTTGGATAGTTGTGAAAGAGTCAAATGGCTCTCCTCAAGCGTATTCAACAAGGGGCTGAAGGATGCCCAGAA
GGTACCCCATTGTATGGGATCTGATCTGGGGCCTCGGTGCACATGCTTTACATGTGTTTAGTCGAGGTTAAAAAAACGTCTAGGCC
CCCCGAACCACGGGGACGTGGTTTTCCTTTGAAAAACACGATGATAATATGGCCACAACCATGactagtGTGAGCAGAAGACCCTG
GCTGCTGGCCCTGGCCCTGGCCGTGGCCCTGGCCGCCGGCAGCGCCGGCGCCAGCACCGGCAGCGACGCCACCGTGCCCGTGGCCA
CCCAGGACGGCCCCGACTACGTGTTCCACAGAGCCCACGAGAGAATGCTGTTCCAGACCAGCTACACCCTGGAGAACAACGGCAGC
GTGATCTGCATCCCCAACAACGGCCAGTGCTTCTGCCTGGCCTGGCTGAAGAGTAACGGCACCAACGCCGAGAAGCTGGCCGCCAA
CATCCTGCAGTGGATCACCTTCGCCCTGAGCGCCCTGTGCCTGATGTTCTACGGCTACCAGACCTGGAAGAGTACCTGCGGCTGGG
AGGAGATCTACGTGGCCACCATCGAGATGATCAAGTTCATCATAGAGTACTTCCACGAGTTCGACGAGCCCGCCGTGATCTACAGC
AGCAACGGCAACAAGACCGTGTGGCTGAGATACGCCGAGTGGCTGCTGACCTGCCCCGTGGTCCTGATCCACCTGAGCAACCTGAC
CGGCCTGGCCAACGACTACAACAAGAGAACCATGGGCCTGCTGGTGAGCGACATCGGCACCATCGTGTGGGGCACCACCGCCGCCC
TGAGCAAGGGCTACGTGAGAGTGATCTTCTTCCTGATGGGCCTGTGCTACGGCATCTACACCTTCTTCAACGCCGCCAAGGTGTAC
ATCGAGGCCTACCACACCGTGCCCAAGGGCAGATGCAGACAGGTGGTGACCGGCATGGCCTGGCTGTTCTTCGTGAGCTGGGGCAT
GTTCCCCATCCTGTTCATCCTGGGCCCCGAGGGCTTCGGCGTGCTGAGCGTGTACGGCAGCACCGTGGGCCACACCATCATCGACC
TGATGAGCAAGAACTGCTGGGGCCTGCTGGGCCACTACCTGAGAGTGCTGATCCACGAGCACATCCTGATCCACGGCGACATCAGA
AAGACCACCAAGCTGAACATCGGCGGCACCGAGATCGAGGTGGAGACCCTGGTGGAGGACGAGGCCGAGGCCGGCGCCGTGAACAA
GGGCACCGGCAAGTACGAGAGCAGCctcgagATGGTGAGCAAGGGCGAGGAGGATAACATGGCCATCATCAAGGAGTTCATGCGCT
TCAAGGTGCACATGGAGGGCTCCGTGAACGGCCACGAGTTCGAGATCGAGGGCGAGGGCGAGGGCCGCCCCTACGAGGGCACCCAG
ACCGCCAAGCTGAAGGTGACCAAGGGTGGCCCCCTGCCCTTCGCCTGGGACATCCTGTCCCCTCAGTTCATGTACGGCTCCAAGGC
CTACGTGAAGCACCCCGCCGACATCCCCGACTACTTGAAGCTGTCCTTCCCCGAGGGCTTCAAGTGGGAGCGCGTGATGAACTTCG
AGGACGGCGGCGTGGTGACCGTGACCCAGGACTCCTCCCTGCAGGACGGCGAGTTCATCTACAAGGTGAAGCTGCGCGGCACCAAC
TTCCCCTCCGACGGCCCCGTAATGCAGAAGAAGACCATGGGCTGGGAGGCCTCCTCCGAGCGGATGTACCCCGAGGACGGCGCCCT
GAAGGCGCAGATCAAGCAGAGGCTGAAGCTGAAGGACGGCGGCCACTACGACGCTGAGGTCAAGACCACCTACAAGGCCAAGAAGC
CCGTGCAGCTGCCCGGCGCCTACAACGTCAACATCAAGTTGGACATCACCTCCCACAACGAGGACTACACCATCGTGGAACAGTAC
GAACGCGCCGAGGGCCGCCACTCCACCGGCGGCATGGACGAGCTGTACAAGTAAtctaga
                                                         XbaI

FIG. 1A

Trial 1:
20s, 470nm, single pulse, 2h incubation

Trial 2:
20s blue 470nm, 40s dark, pulse train for 10min

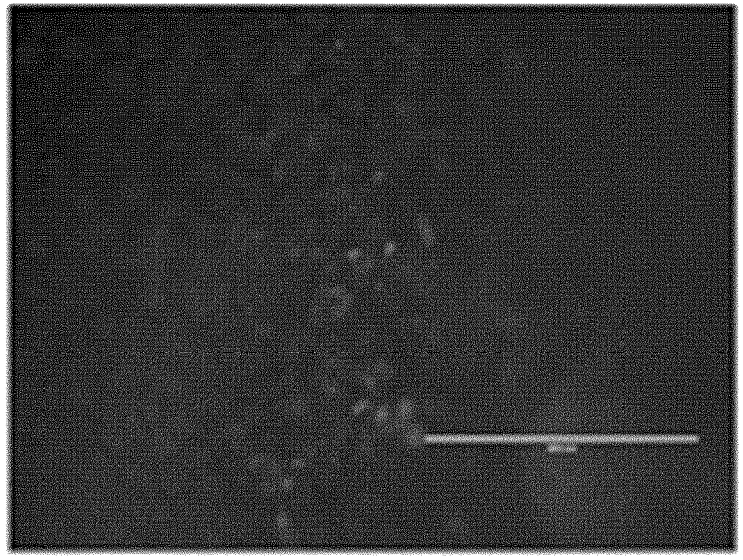

FIG. 6B

MSRRPWLLALALAVALAAGSAGASTGSDATVPVATQDGPDYVFHRAHERMLFQTSYTLEN
NGSVICIPNNGQCFCLAWLKSNGTNAEKLAANILQWITFALSALCLMFYGYQTWKSTCGW
EEIYVATIEMIKFIIEYFHEFDEPAVIYSSNGNKTVWLRYAEWLLTCPVILIHLSNLTGL
ANDYNKRTMGLLVSDIGTIVWGTTAALSKGYVRVIFFLMGLCYGIYTFFNAAKVYIEAYH
TVPKGICRDLVRYLAWLYFCSWAMFPVLFLLGPEGFGHINQFNSAIAHAILDLASKNAWS
MMGHFLRVKIHEHILLYGDIRKKQKVNVAGQEMEVETMVHEEDDETQKVPTAKYANRDSF
IIMRDRLKEKGFETRASLDGDPNGDAEANAAAGGKPGMEMGKMTGMGMGMGAGMGMATID
SGRVILAVPDISMVDFFREQFARLPVPYELVPALGAENTLQLVQQAQSLGGCDFVLMHPE
FLRDRSPTGLLPRLKMGGQRAAAFGWAAIGPMRDLIEGSGVDGWLEGPSFGAGINQQALV
ALINRMQQAKKMGMMGGMGMGMGGGMGMGMGMGMGMAPSMNAGMTGGMGGASMGGAVMGM
GMGMQPMQQAMPAMSPMMTQQPSMMSQPSAMSAGGAMQAMGGVMPSPAPGGRVGTNPLFG
SAPSPLSSQPGISPGMATPPAATAAPAAGGSEAEMLQQLMSEINRLKNELGE

FIG. 7A

```
  1 mdyggalsav grellfvtnp vvvngsvlvp edqcycagwi esrgtngaqt asnvlqwlaa
 61 gfsilllmfy ayqtwkstcg weeiyvcaie mvkvilefff efknpsmlyl atghrvqwlr
121 yaewlltcpv ilihlsnltg lsndysrrtm gllvsdigti vwgatsamat gyvkviffcl
181 glcygantff haakayiegy htvpkgrcrq vvtgmawlff vswgmfpilf ilgpegfgvl
241 svygstvght iidlmskncw gllghylrvl ihehilihgd irkttklnig gteievetlv
301 edeaeagavn kgtgkyasre sflvmrdkmk ekgidvrasl dnskeveqeq aaraammmmn
361 gngmgmgmgm ngmngmggmn gmaggakpgl eltpqlqpgr vilavpdism vdffreqfaq
421 lsvtyelvpa lgadntlalv tqaqnlggvd fvlihpeflr drsstsilsr lrgagqrvaa
481 fgwaqlgpmr dliesanldg wlegpsfgqg ilpahivalv akmqqmrkmq qmqqigmmtg
541 gmngmgggmg ggmngmgggn gmnnmgngmg ggmgngmggn gmngmgggng mnnmggngma
601 gngmgggmgg ngmggsmngm ssgvvanvtp saaggmggmm nggmaapqsp gmnggrlgtn
661 plfnaapspl ssqlgaeagm gsmggmggms gmggmggmgg mggagaattq aaggnaeaem
721 lqnlmneinr lkrelge
```

FIG. 7B

SEQUENCE LISTING

<160> NUMBER OF SEQ ID NOS: 29

<210> SEQ ID NO 1
<211> LENGTH: 4
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa is any naturally occurring amino acid

<400> SEQUENCE: 1

Arg Xaa Lys Arg
1

<210> SEQ ID NO 2
<211> LENGTH: 20
<212> TYPE: PRT
<213> ORGANISM: Homo sapiens

<400> SEQUENCE: 2

Met His Trp Gly Thr Leu Cys Gly Phe Leu Trp Leu Trp Pro Tyr Leu
1               5                   10                  15

Phe Tyr Gln Ala
            20

<210> SEQ ID NO 3
<211> LENGTH: 2726
<212> TYPE: DNA
<213> ORGANISM: Artificial Sequence
<220> FEATURE:
<223> OTHER INFORMATION: Synthetic construct

<400> SEQUENCE: 3
gcggccgcgc caccatgcat tggggaaccc tgtgcggatt cttgtggctt tggccctatc      60
ttttctatgt ccaagctttt gtgaaccaac acctgtgcgg ctcacacctg gtggaagctc    120
tctacctagt gtgcggggaa cgaggcttct tctacacacc cgtaccaagc gggaggcag     180 aggacctgca ggtggggcag gtggagctgg gcggggggccc tggtgcaggc agcctgcagc   240
ccttggccct ggaggggtcc cgtcagaagc gtggcattgt ggaacaatgc tgtaccagca   300
tctgctccct ctaccagctg gagaactact gcaactagcg tacgccccc cccctaacgt    360 tactggccga agccgcttgg aataaggccg gtgtgcgttt gtctatatgt tattttccac   420
catattgccg tcttttggca atgtgagggc ccggaaacct ggccctgtct tcttgacgag   480
cattcctagg ggtctttccc ctctcgccaa aggaatgcaa ggtctgttga atgtcgtgaa   540
ggaagcagtt cctctggaag cttcttgaag acaaacaacg tctgtagcga ccctttgcag   600
gcagcggaac cccccacctg gcgacaggtg cctctgcggc caaaagccac gtgtataaga   660
tacacctgca aaggcggcac aaccccagtg ccacgttgtg agttggatag ttgtggaaag   720
agtcaaatgg ctctcctcaa gcgtattcaa caaggggctg aaggatgccc agaaggtacc   780
ccattgtatg ggatctgatc tggggcctcg gtgcacatgc tttacatgtg tttagtcgag   840
gttaaaaaaa cgtctaggcc cccgaaacca cggggacgtg gttttccttt gaaaaacacg   900
atgataatat ggccacaacc atgactagtg tgagcagaag accctggctg ctggccctgg   960
ccctggccgt ggccctggcc gccggcagcg ccggcgccag caccggcagc gacgccaccg  1020
tgcccgtggc cacccaggac ggccccgact acgtgttcca cagagcccac gagagaatgc  1080
tgttccagac cagctacacc ctggagaaca acggcagcgt gatctgcatc cccaacaacg  1140

-continued

```
gccagtgctt ctgcctggcc tggctgaaga gtaacggcac caacgccgag aagctggccg    1200
ccaacatcct gcagtggatc accttcgccc tgagcgccct gtgcctgatg ttctacggct    1260
accagacctg gaagagtacc tgcggctggg aggagatcta cgtggccacc atcgagatga    1320
tcaagttcat catagagtac ttccacgagt tcgacgagcc cgccgtgatc tacagcagca    1380
acggcaacaa gaccgtgtgg ctgagatacg ccgagtggct gctgacctgc ccgtggtcc     1440 tgatccacct gagcaacctg accggcctgg ccaacgacta caacaagaga ccatgggcc     1500 tgctggtgag cgacatcggc accatcgtgt ggggcaccac cgccgccctg agcaagggct    1560
acgtgagagt gatcttcttc ctgatgggcc tgtgctacgg catctacacc ttcttcaacg    1620
ccgccaaggt gtacatcgag gcctaccaca ccgtgcccaa gggcagatgc agacaggtgg    1680
tgaccggcat ggcctggctg ttcttcgtga gctgggcat gttccccatc ctgttcatcc     1740
tgggccccga gggcttcggc gtgctgagcg tgtacggcag caccgtgggc cacaccatca    1800
tcgacctgat gagcaagaac tgctgggccc tgctgggcca ctacctgaga gtgctgatcc    1860
acgagcacat cctgatccac ggcgacatca gaaagaccac caagctgaac atcggcggca    1920
ccgagatcga ggtggagacc ctggtggagg acgaggccga ggccggcgcc gtgaacaagg    1980
gcaccggcaa gtacgagagc agcctcgaga tggtgagcaa gggcgaggag gataacatgg    2040
ccatcatcaa ggagttcatg cgcttcaagg tgcacatgga gggctccgtg aacggccacg    2100
agttcgagat cgagggcgag ggcgagggcc gcccctacga gggcacccag accgccaagc    2160
tgaaggtgac caagggtggc cccctgccct cgcctggga catcctgtcc cctcagttca    2220
tgtacggctc caaggcctac gtgaagcacc ccgccgacat ccccgactac ttgaagctgt    2280
ccttccccga gggcttcaag tgggagcgcg tgatgaactt cgaggacggc ggcgtggtga    2340
ccgtgaccca ggactcctcc ctgcaggacg gcgagttcat ctacaaggtg aagctgcgcg    2400
gcaccaactt ccctccgac ggccccgtaa tgcagaagaa gaccatgggc tgggaggcct     2460
cctccgagcg gatgtacccc gaggacggcg ccctgaaggg cgagatcaag cagaggctga    2520
agctgaagga cggcggccac tacgacgctg aggtcaagac cacctacaag gccaagaagc    2580
ccgtgcagct gcccggcgcc tacaacgtca acatcaagtt ggacatcacc tcccacaacg    2640
aggactacac catcgtggaa cagtacgaac gcgccgaggg ccgccactcc accggcggca    2700
tggacgagct gtacaagtaa tctaga                                         2726
```

<210> SEQ ID NO 4
<211> LENGTH: 32
<212> TYPE: PRT
<213> ORGANISM: Homo sapiens

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Arg Thr Lys Arg
            20                  25                  30

<210> SEQ ID NO 5
<211> LENGTH: 33
<212> TYPE: PRT
<213> ORGANISM: Homo sapiens

<400> SEQUENCE: 5

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Arg Gln Lys
            20                  25                  30

Arg

<210> SEQ ID NO 6
<211> LENGTH: 21
<212> TYPE: PRT
<213> ORGANISM: Homo sapiens

<400> SEQUENCE: 6

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 7
<211> LENGTH: 106
<212> TYPE: PRT
<213> ORGANISM: Homo sapiens

<400> SEQUENCE: 7

Met His Trp Gly Thr Leu Cys Gly Phe Leu Trp Leu Trp Pro Tyr Leu
1               5                   10                  15

Phe Tyr Gln Ala Phe Val Asn Gln His Leu Cys Gly Ser His Leu Val
            20                  25                  30

Glu Ala Leu Tyr Leu Val Cys Gly Glu Arg Gly Phe Phe Tyr Thr Pro
        35                  40                  45

Arg Thr Lys Arg Glu Ala Glu Asp Leu Gln Val Gly Gln Val Glu Leu
    50                  55                  60

Gly Gly Gly Pro Gly Ala Gly Ser Leu Gln Pro Leu Ala Leu Glu Gly
65                  70                  75                  80

Ser Arg Gln Lys Arg Gly Ile Val Glu Gln Cys Cys Thr Ser Ile Cys
                85                  90                  95

Ser Leu Tyr Gln Leu Glu Asn Tyr Cys Asn
            100                 105

<210> SEQ ID NO 8
<211> LENGTH: 712
<212> TYPE: PRT
<213> ORGANISM: Chlamydomonas reinhardtii

<400> SEQUENCE: 8

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

```
Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Ile Leu Ile His Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Ile Cys Arg Asp Leu Val Arg Tyr Leu Ala Trp
                245                 250                 255

Leu Tyr Phe Cys Ser Trp Ala Met Phe Pro Val Leu Phe Leu Leu Gly
            260                 265                 270

Pro Glu Gly Phe Gly His Ile Asn Gln Phe Asn Ser Ala Ile Ala His
        275                 280                 285

Ala Ile Leu Asp Leu Ala Ser Lys Asn Ala Trp Ser Met Met Gly His
    290                 295                 300

Phe Leu Arg Val Lys Ile His Glu His Ile Leu Leu Tyr Gly Asp Ile
305                 310                 315                 320

Arg Lys Lys Gln Lys Val Asn Val Ala Gly Gln Glu Met Glu Val Glu
                325                 330                 335

Thr Met Val His Glu Glu Asp Glu Thr Gln Lys Val Pro Thr Ala
            340                 345                 350

Lys Tyr Ala Asn Arg Asp Ser Phe Ile Ile Met Arg Asp Arg Leu Lys
    355                 360                 365

Glu Lys Gly Phe Glu Thr Arg Ala Ser Leu Asp Gly Asp Pro Asn Gly
370                 375                 380

Asp Ala Glu Ala Asn Ala Ala Ala Gly Gly Lys Pro Gly Met Glu Met
385                 390                 395                 400

Gly Lys Met Thr Gly Met Gly Met Gly Ala Gly Met Gly Met
                405                 410                 415

Ala Thr Ile Asp Ser Gly Arg Val Ile Leu Ala Val Pro Asp Ile Ser
                420                 425                 430

Met Val Asp Phe Phe Arg Glu Gln Phe Ala Arg Leu Pro Val Pro Tyr
            435                 440                 445

Glu Leu Val Pro Ala Leu Gly Ala Glu Asn Thr Leu Gln Leu Val Gln
    450                 455                 460

Gln Ala Gln Ser Leu Gly Gly Cys Asp Phe Val Leu Met His Pro Glu
465                 470                 475                 480

Phe Leu Arg Asp Arg Ser Pro Thr Gly Leu Leu Pro Arg Leu Lys Met
                485                 490                 495

Gly Gly Gln Arg Ala Ala Ala Phe Gly Trp Ala Ala Ile Gly Pro Met
            500                 505                 510

Arg Asp Leu Ile Glu Gly Ser Gly Val Asp Gly Trp Leu Glu Gly Pro
        515                 520                 525

Ser Phe Gly Ala Gly Ile Asn Gln Gln Ala Leu Val Ala Leu Ile Asn
    530                 535                 540
```

-continued

```
Arg Met Gln Gln Ala Lys Lys Met Gly Met Met Gly Met Gly Met
545                 550                 555                 560

Gly Met Gly Gly Gly Met Gly Met Gly Met Gly Met Gly Met
            565                 570                 575

Ala Pro Ser Met Asn Ala Gly Met Thr Gly Gly Met Gly Gly Ala Ser
            580                 585                 590

Met Gly Gly Ala Val Met Gly Met Gly Met Gly Met Gln Pro Met Gln
        595                 600                 605

Gln Ala Met Pro Ala Met Ser Pro Met Met Thr Gln Gln Pro Ser Met
    610                 615                 620

Met Ser Gln Pro Ser Ala Met Ser Ala Gly Gly Ala Met Gln Ala Met
625                 630                 635                 640

Gly Gly Val Met Pro Ser Pro Ala Pro Gly Gly Arg Val Gly Thr Asn
            645                 650                 655

Pro Leu Phe Gly Ser Ala Pro Ser Pro Leu Ser Ser Gln Pro Gly Ile
            660                 665                 670

Ser Pro Gly Met Ala Thr Pro Pro Ala Ala Thr Ala Ala Pro Ala Ala
            675                 680                 685

Gly Gly Ser Glu Ala Glu Met Leu Gln Gln Leu Met Ser Glu Ile Asn
            690                 695                 700

Arg Leu Lys Asn Glu Leu Gly Glu
705                 710

<210> SEQ ID NO 9
<211> LENGTH: 737
<212> TYPE: PRT
<213> ORGANISM: Chlamydomonas reinhardtii

<400> SEQUENCE: 9

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205
```

```
Arg Gln Val Val Thr Gly Met Ala Trp Leu Phe Phe Val Ser Trp Gly
    210                 215                 220
Met Phe Pro Ile Leu Phe Ile Leu Gly Pro Glu Gly Phe Gly Val Leu
225                 230                 235                 240
Ser Val Tyr Gly Ser Thr Val Gly His Thr Ile Ile Asp Leu Met Ser
                245                 250                 255
Lys Asn Cys Trp Gly Leu Leu Gly His Tyr Leu Arg Val Leu Ile His
            260                 265                 270
Glu His Ile Leu Ile His Gly Asp Ile Arg Lys Thr Thr Lys Leu Asn
        275                 280                 285
Ile Gly Gly Thr Glu Ile Glu Val Glu Thr Leu Val Glu Asp Glu Ala
290                 295                 300
Glu Ala Gly Ala Val Asn Lys Gly Thr Gly Lys Tyr Ala Ser Arg Glu
305                 310                 315                 320
Ser Phe Leu Val Met Arg Asp Lys Met Lys Glu Lys Gly Ile Asp Val
                325                 330                 335
Arg Ala Ser Leu Asp Asn Ser Lys Glu Val Glu Gln Glu Gln Ala Ala
            340                 345                 350
Arg Ala Ala Met Met Met Met Asn Gly Asn Gly Met Gly Met Gly Met
        355                 360                 365
Gly Met Asn Gly Met Asn Gly Met Gly Gly Met Asn Gly Met Ala Gly
370                 375                 380
Gly Ala Lys Pro Gly Leu Glu Leu Thr Pro Gln Leu Gln Pro Gly Arg
385                 390                 395                 400
Val Ile Leu Ala Val Pro Asp Ile Ser Met Val Asp Phe Phe Arg Glu
                405                 410                 415
Gln Phe Ala Gln Leu Ser Val Thr Tyr Glu Leu Val Pro Ala Leu Gly
            420                 425                 430
Ala Asp Asn Thr Leu Ala Leu Val Thr Gln Ala Gln Asn Leu Gly Gly
        435                 440                 445
Val Asp Phe Val Leu Ile His Pro Glu Phe Leu Arg Asp Arg Ser Ser
450                 455                 460
Thr Ser Ile Leu Ser Arg Leu Arg Gly Ala Gly Gln Arg Val Ala Ala
465                 470                 475                 480
Phe Gly Trp Ala Gln Leu Gly Pro Met Arg Asp Leu Ile Glu Ser Ala
                485                 490                 495
Asn Leu Asp Gly Trp Leu Glu Gly Pro Ser Phe Gly Gln Gly Ile Leu
            500                 505                 510
Pro Ala His Ile Val Ala Leu Val Ala Lys Met Gln Gln Met Arg Lys
        515                 520                 525
Met Gln Gln Met Gln Gln Ile Gly Met Met Thr Gly Gly Met Asn Gly
530                 535                 540
Met Gly Gly Gly Met Gly Gly Met Asn Gly Met Gly Gly Asn
545                 550                 555                 560
Gly Met Asn Asn Met Gly Asn Gly Met Gly Gly Met Gly Asn Gly
                565                 570                 575
Met Gly Gly Asn Gly Met Asn Gly Met Gly Gly Asn Gly Met Asn
            580                 585                 590
Asn Met Gly Gly Asn Gly Met Ala Gly Asn Gly Met Gly Gly Gly Met
        595                 600                 605
Gly Gly Asn Gly Met Gly Gly Ser Met Asn Gly Met Ser Ser Gly Val
610                 615                 620
```

```
Val Ala Asn Val Thr Pro Ser Ala Ala Gly Gly Met Gly Gly Met Met
625                 630                 635                 640

Asn Gly Gly Met Ala Ala Pro Gln Ser Pro Gly Met Asn Gly Gly Arg
            645                 650                 655

Leu Gly Thr Asn Pro Leu Phe Asn Ala Ala Pro Ser Pro Leu Ser Ser
            660                 665                 670

Gln Leu Gly Ala Glu Ala Gly Met Gly Ser Met Gly Gly Met Gly Gly
            675                 680                 685

Met Ser Gly Met Gly Gly Met Gly Gly Met Gly Gly Met Gly Gly Ala
            690                 695                 700

Gly Ala Ala Thr Thr Gln Ala Ala Gly Gly Asn Ala Glu Ala Glu Met
705                 710                 715                 720

Leu Gln Asn Leu Met Asn Glu Ile Asn Arg Leu Lys Arg Glu Leu Gly
                725                 730                 735

Glu

<210> SEQ ID NO 10
<211> LENGTH: 359
<212> TYPE: PRT
<213> ORGANISM: Chlamydomonas reinhardtii

<400> SEQUENCE: 10

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
            35                  40                  45

Glu Arg Met Leu Phe Gln Thr Ser Tyr Thr Leu Glu Asn Asn Gly Ser
50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Ile Thr Phe Ala Leu Ser Ala Leu Cys Leu Met Phe Tyr Gly Tyr
            100                 105                 110

Gln Thr Trp Lys Ser Thr Cys Gly Trp Glu Glu Ile Tyr Val Ala Thr
            115                 120                 125

Ile Glu Met Ile Lys Phe Ile Ile Glu Tyr Phe His Glu Phe Asp Glu
130                 135                 140

Pro Ala Val Ile Tyr Ser Ser Asn Gly Asn Lys Thr Val Trp Leu Arg
145                 150                 155                 160

Tyr Ala Glu Trp Leu Leu Thr Cys Pro Val Val Leu Ile His Leu Ser
                165                 170                 175

Asn Leu Thr Gly Leu Ala Asn Asp Tyr Asn Lys Arg Thr Met Gly Leu
            180                 185                 190

Leu Val Ser Asp Ile Gly Thr Ile Val Trp Gly Thr Thr Ala Ala Leu
            195                 200                 205

Ser Lys Gly Tyr Val Arg Val Ile Phe Phe Leu Met Gly Leu Cys Tyr
210                 215                 220

Gly Ile Tyr Thr Phe Phe Asn Ala Ala Lys Val Tyr Ile Glu Ala Tyr
225                 230                 235                 240

His Thr Val Pro Lys Gly Arg Cys Arg Gln Val Val Thr Gly Met Ala
                245                 250                 255
```

Trp Leu Phe Phe Val Ser Trp Gly Met Phe Pro Ile Leu Phe Ile Leu
            260                 265                 270

Gly Pro Glu Gly Phe Gly Val Leu Ser Val Tyr Gly Ser Thr Val Gly
        275                 280                 285

His Thr Ile Ile Asp Leu Met Ser Lys Asn Cys Trp Gly Leu Leu Gly
    290                 295                 300

His Tyr Leu Arg Val Leu Ile His Glu His Ile Leu Ile His Gly Asp
305                 310                 315                 320

Ile Arg Lys Thr Thr Lys Leu Asn Ile Gly Thr Glu Ile Glu Val
                325                 330                 335

Glu Thr Leu Val Glu Asp Glu Ala Glu Ala Gly Ala Val Asn Lys Gly
            340                 345                 350

Thr Gly Lys Tyr Glu Ser Ser
        355

<210> SEQ ID NO 11
<211> LENGTH: 837
<212> TYPE: PRT
<213> ORGANISM: Volvox carteri

<400> SEQUENCE: 11

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
            20                  25                  30

Gly Trp Leu Arg Ser Arg Gly Thr Ser Ile Glu Lys Thr Ile Ala Ile
        35                  40                  45

Thr Leu Gln Trp Val Val Phe Ala Leu Ser Val Ala Cys Leu Gly Trp
    50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
            100                 105                 110

Trp Met Arg Tyr Gly Glu Trp Leu Leu Thr Cys Pro Val Leu Leu Ile
        115                 120                 125

His Leu Ser Asn Leu Thr Gly Leu Lys Asp Asp Tyr Ser Lys Arg Thr
    130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
            180                 185                 190

Glu Ala Phe His Thr Val Pro Lys Gly Ile Cys Arg Glu Leu Val Arg
        195                 200                 205

Val Met Ala Trp Thr Phe Phe Val Ala Trp Gly Met Phe Pro Val Leu
    210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
            260                 265                 270

```
Tyr Gly Asp Ile Arg Lys Lys Gln Lys Ile Thr Ile Ala Gly Gln Glu
        275                 280                 285

Met Glu Val Glu Thr Leu Val Ala Glu Glu Asp Thr Val Lys
290                 295                 300

Gln Ser Thr Ala Lys Tyr Ala Ser Arg Asp Ser Phe Ile Thr Met Arg
305                 310                 315                 320

Asn Arg Met Arg Glu Lys Gly Leu Glu Val Arg Ala Ser Leu Asp Ala
                325                 330                 335

Gly Gly Gly Asp Ser Gly Met Glu Ala Gly Gly Gly Ala Ala His
                340                 345                 350

Ala Gln Pro His Met Ala Lys Pro Gly Thr Glu Leu Gly Lys Thr Met
                355                 360                 365

Ser Ala Ser Phe Thr Asn Gly Ala Ala Thr Ser Leu Glu Pro Gly Arg
        370                 375                 380

Val Ile Leu Ala Val Pro Asp Ile Ser Met Val Asp Phe Phe Arg Glu
385                 390                 395                 400

Gln Phe Ala Gln Leu Pro Val Pro Tyr Glu Val Val Pro Ala Leu Gly
                405                 410                 415

Ala Glu Asn Thr Val Gln Leu Val Gln Gln Ala Ala Met Leu Gly Gly
                420                 425                 430

Cys Asp Phe Val Leu Met His Pro Glu Phe Leu Arg Asp Arg Gly Pro
                435                 440                 445

Thr Gly Leu Leu Pro Gln Val Lys Met Met Gly Gln Arg Thr Ala Ala
        450                 455                 460

Phe Gly Trp Ser Gln Met Gly Pro Met Arg Asp Leu Ile Glu Ser Ser
465                 470                 475                 480

Gly Val Gly Ala Trp Leu Glu Gly Pro Ser Phe Gly Ser Gly Ile Ser
                485                 490                 495

Gln Ala Ala Leu Gln Gln Leu Val Val Lys Met Gln Gln Ala Lys Arg
                500                 505                 510

Met Ala Ala Met Gly Ser Met Met Gly Gly Met Gly Asn Gly Met
                515                 520                 525

Gly Met Gly Met Gly Met Gly Met Gly Met Gly Met Asn Gly Met
530                 535                 540

Gly Asn Gly Met Gly Met Gly Asn Gly Met Gly Asn Gly Met Gly Met
545                 550                 555                 560

Gly Asn Gly Met Gly Asn Gly Met Gly Met Gly Asn Gly Met Gly Met
                565                 570                 575

Gly Asn Gly Met Gly Asn Gly Met Gly Met Gly Asn Gly Met
                580                 585                 590

Gly Asn Gly Met Gly Asn Gly Met Gly Met Gly Asn Gly Met Gly Asn
                595                 600                 605

Gly Met Gly Asn Gly Met Gly Asn Gly Met Gly Asn Gly Met Gly Asn
        610                 615                 620

Gly Met Gly Met Gly Asn Gly Met Gly Met Gly Asn Gly Met Gly Asn
625                 630                 635                 640

Gly Met Gly Asn Gly Met Gly Asn Gly Met Gly Asn Gly Met Gly Met
                645                 650                 655

Met Thr Pro Gly Ala Met Gly Met Gly Met Gly Gly Met Gly Asn Leu
                660                 665                 670

Ala Ala Ala Ala Gly Asn Ala Met Tyr Gly Gly Gly Gly Gly Gly
                675                 680                 685
```

```
Gly Ser Thr Met Gly Ser Gly Asn Ala Ala Met Met Thr Gly Leu Val
        690                 695                 700

Met Gly Gly Gly Asn Gly Val Gly Ala Gly Pro Gly Gly Val Val Ala
705                 710                 715                 720

Asn Leu Gly Ser Ser Ala Leu Gln Pro Gln Ser Gln Met Met Gly Gly
                725                 730                 735

Gly Asn Val Val Gly Met Ser Ser Pro Gln Leu Gln Leu Gln Gln Ser
                740                 745                 750

Ser Ser Met Pro Leu Gly Gly Leu Ala Pro Asn Arg Ile Gly Asn Asn
        755                 760                 765

Pro Leu Phe Gly Ala Ala Pro Ser Pro Leu His Ser Gln Pro Gly Ala
770                 775                 780

Ser Pro Thr Gly Leu Ser Ser Pro Gln Leu Gly Met Gly Ala Met Leu
785                 790                 795                 800

Pro Ala Gly Thr Ser Val Gly Ala Gly Gly Ser Val Gly Pro Thr
                805                 810                 815

Glu Thr Asp Met Leu Gln Gln Leu Met Thr Glu Ile Asn Arg Leu Lys
                820                 825                 830

Asp Glu Leu Gly Glu
        835

<210> SEQ ID NO 12
<211> LENGTH: 747
<212> TYPE: PRT
<213> ORGANISM: Volvox carteri

<400> SEQUENCE: 12

Met Asp His Pro Val Ala Arg Ser Leu Ile Gly Ser Ser Tyr Thr Asn
1               5                   10                  15

Leu Asn Asn Gly Ser Ile Val Ile Pro Ser Asp Ala Cys Phe Cys Met
                20                  25                  30

Lys Trp Leu Lys Ser Lys Gly Ser Pro Val Ala Leu Lys Met Ala Asn
        35                  40                  45

Ala Leu Gln Trp Ala Ala Phe Ala Leu Ser Val Ile Ile Leu Ile Tyr
50                  55                  60

Tyr Ala Tyr Ala Thr Trp Arg Thr Thr Cys Gly Trp Glu Glu Val Tyr
65                  70                  75                  80

Val Cys Cys Val Glu Leu Thr Lys Val Val Ile Glu Phe Phe His Glu
                85                  90                  95

Phe Asp Glu Pro Gly Met Leu Tyr Leu Ala Asn Gly Asn Arg Val Leu
                100                 105                 110

Trp Leu Arg Tyr Gly Glu Trp Leu Leu Thr Cys Pro Val Ile Leu Ile
        115                 120                 125

His Leu Ser Asn Leu Thr Gly Leu Lys Asp Asp Tyr Asn Lys Arg Thr
130                 135                 140

Met Arg Leu Leu Val Ser Asp Val Gly Thr Ile Val Trp Gly Ala Thr
145                 150                 155                 160

Ala Ala Met Ser Thr Gly Tyr Ile Lys Val Ile Phe Phe Leu Leu Gly
                165                 170                 175

Cys Met Tyr Gly Ala Asn Thr Phe Phe His Ala Ala Lys Val Tyr Ile
                180                 185                 190

Glu Ser Tyr His Thr Val Pro Lys Gly Leu Cys Arg Gln Leu Val Arg
        195                 200                 205

Ala Met Ala Trp Leu Phe Phe Val Ser Trp Gly Met Phe Pro Val Leu
210                 215                 220
```

```
Phe Leu Leu Gly Pro Glu Gly Phe Gly His Leu Ser Val Tyr Gly Ser
225                 230                 235                 240

Thr Ile Gly His Thr Ile Ile Asp Leu Leu Ser Lys Asn Cys Trp Gly
            245                 250                 255

Leu Leu Gly His Phe Leu Arg Leu Lys Ile His Glu His Ile Leu Leu
        260                 265                 270

Tyr Gly Asp Ile Arg Lys Val Gln Lys Ile Arg Val Ala Gly Glu Glu
    275                 280                 285

Leu Glu Val Glu Thr Leu Met Thr Glu Glu Ala Pro Asp Thr Val Lys
290                 295                 300

Lys Ser Thr Ala Gln Tyr Ala Asn Arg Glu Ser Phe Leu Thr Met Arg
305                 310                 315                 320

Asp Lys Leu Lys Glu Lys Gly Phe Glu Val Arg Ala Ser Leu Asp Asn
                325                 330                 335

Ser Gly Ile Asp Ala Val Ile Asn His Asn Asn Tyr Asn Asn Ala
            340                 345                 350

Leu Ala Asn Ala Ala Ala Ala Val Gly Lys Pro Gly Met Glu Leu Ser
        355                 360                 365

Lys Leu Asp His Val Ala Ala Asn Ala Ala Gly Met Gly Gly Ile Ala
370                 375                 380

Asp His Val Ala Thr Thr Ser Gly Ala Ile Ser Pro Gly Arg Val Ile
385                 390                 395                 400

Leu Ala Val Pro Asp Ile Ser Met Val Asp Tyr Phe Arg Glu Gln Phe
                405                 410                 415

Ala Gln Leu Pro Val Gln Tyr Glu Val Val Pro Ala Leu Gly Ala Asp
            420                 425                 430

Asn Ala Val Gln Leu Val Val Gln Ala Ala Gly Leu Gly Gly Cys Asp
        435                 440                 445

Phe Val Leu Leu His Pro Glu Phe Leu Arg Asp Lys Ser Ser Thr Ser
450                 455                 460

Leu Pro Ala Arg Leu Arg Ser Ile Gly Gln Arg Val Ala Ala Phe Gly
465                 470                 475                 480

Trp Ser Pro Val Gly Pro Val Arg Asp Leu Ile Glu Ser Ala Gly Leu
                485                 490                 495

Asp Gly Trp Leu Glu Gly Pro Ser Phe Gly Leu Gly Ile Ser Leu Pro
            500                 505                 510

Asn Leu Ala Ser Leu Val Leu Arg Met Gln His Ala Arg Lys Met Ala
        515                 520                 525

Ala Met Leu Gly Gly Met Gly Gly Met Leu Gly Ser Asn Leu Met Ser
530                 535                 540

Gly Ser Gly Gly Val Gly Leu Met Gly Ala Gly Ser Pro Gly Gly Gly
545                 550                 555                 560

Gly Gly Ala Met Gly Val Gly Met Thr Gly Met Gly Met Val Gly Thr
                565                 570                 575

Asn Ala Met Gly Arg Gly Ala Val Gly Asn Ser Val Ala Asn Ala Ser
            580                 585                 590

Met Gly Gly Gly Ser Ala Gly Met Gly Met Gly Met Met Gly Met Val
        595                 600                 605

Gly Ala Gly Val Gly Gly Gln Gln Gln Met Gly Ala Asn Gly Met Gly
610                 615                 620

Pro Thr Ser Phe Gln Leu Gly Ser Asn Pro Leu Tyr Asn Thr Ala Pro
625                 630                 635                 640
```

```
Ser Pro Leu Ser Ser Gln Pro Gly Gly Asp Ala Ser Ala Ala Ala Ala
                    645             650             655

Ala Ala Ala Ala Ala Ala Thr Gly Ala Ala Ser Asn Ser Met Asn
        660             665             670

Ala Met Gln Ala Gly Gly Ser Val Arg Asn Ser Gly Ile Leu Ala Gly
            675             680             685

Gly Leu Gly Ser Met Met Gly Pro Pro Gly Ala Pro Ala Ala Pro Thr
        690             695             700

Ala Ala Ala Thr Ala Ala Pro Ala Val Thr Met Gly Ala Pro Gly Gly
705             710             715             720

Gly Gly Ala Ala Ala Ser Glu Ala Glu Met Leu Gln Gln Leu Met Ala
            725             730             735

Glu Ile Asn Arg Leu Lys Ser Glu Leu Gly Glu
            740             745

<210> SEQ ID NO 13
<211> LENGTH: 217
<212> TYPE: PRT
<213> ORGANISM: Pleodorina starrii

<400> SEQUENCE: 13

Gly Thr Asn Ala Glu Lys Leu Ala Ala Asn Ile Leu Gln Trp Gly Ala
1               5                   10                  15

Leu Ala Leu Cys Val Met Phe Ser Gly Tyr Gln Thr Trp Lys Ser Thr
            20                  25                  30

Cys Gly Trp Glu Glu Ile Tyr Val Ala Lys Ile Glu Met Ile Lys Phe
        35                  40                  45

Ile Ile Glu Tyr Phe His Glu Phe Asp Glu Pro Ala Val Ile Tyr Ser
    50                  55                  60

Phe Asn Gly Asn Lys Thr Val Trp Leu Arg Tyr Ala Glu Trp Leu Leu
65                  70                  75                  80

Thr Cys Val Ile Leu Ile His Leu Ser Asn Leu Thr Gly Leu Ala Asn
                85                  90                  95

Asp Tyr Asn Asn Arg Thr Met Gly Leu Leu Val Ser Asp Val Gly Thr
            100                 105                 110

Ser Val Trp Gly Thr Thr Ala Ala Leu Ser Lys Gly Tyr Ser Pro Cys
        115                 120                 125

His Phe Leu Pro Asp Leu Ala Tyr Gly Ile Tyr Thr Phe Phe Asn Ala
    130                 135                 140

Ala Lys Val Tyr Ile Glu Ala Tyr His Thr Val Pro Lys Gly Ile Cys
145                 150                 155                 160

Arg Asp Leu Val Arg Tyr Leu Ala Trp Leu Tyr Phe Cys Ser Trp Ala
                165                 170                 175

Ser Phe Pro Val Leu Phe Leu Leu Gly Pro Glu Gly Phe Gly His Ile
            180                 185                 190

Asn Gln Phe Asn Ser Ala Ile Ala His Ala Ile Leu Asp Leu Ala Ser
        195                 200                 205

Lys Asn Ala Trp Ser Val Ile Gly His
    210                 215

<210> SEQ ID NO 14
<211> LENGTH: 227
<212> TYPE: PRT
<213> ORGANISM: Pleodorina starrii

<400> SEQUENCE: 14
```

```
Gly Thr Asn Gly Ala Gln Thr Ala Ser Asn Val Leu Gln Trp Gln Leu
1               5                   10                  15

Ala Ala Gly Phe Ser Ile Leu Leu Met Phe Tyr Ala Tyr Gln Thr
            20                  25                  30

Trp Lys Ser Thr Cys Gly Trp Glu Glu Ile Tyr Val Cys Ala Ile Glu
        35                  40                  45

Met Val Lys Val Ile Leu Glu Phe Phe Phe Glu Phe Lys Asn Pro Ser
50                  55                  60

Met Leu Tyr Leu Ala Thr Gly His Arg Val Gln Trp Leu Arg Tyr Ala
65                  70                  75                  80

Glu Trp Leu Leu Thr Cys Pro Val Ile Leu Ile His Leu Ser Asn Leu
                85                  90                  95

Thr Gly Leu Ser Asn Asp Asp Ser Ser Arg Thr Met Gly Leu Leu Ala
            100                 105                 110

Cys Ser Ile Gly Thr Ile Val Trp Gly Ala Thr Ser Ala Met Ala Ser
        115                 120                 125

Gly Tyr Val Lys Val Ile Phe Phe Cys Leu Gly Val Tyr Cys Ala Asn
        130                 135                 140

Thr Phe Tyr Arg Ala Gln Ala Tyr Ile Lys Gly Tyr His Thr Val Pro
145                 150                 155                 160

Lys Gly Arg Cys Arg Gln Val Val Thr Gly Met Ala Trp Leu Phe Phe
                165                 170                 175

Val Ser Trp Gly Met Phe Pro Ile Leu Phe Ile Leu Gly Pro Glu Gly
            180                 185                 190

Phe Gly Val Leu Ser Val Tyr Gly Ser Thr Val Gly His Thr Ile Ile
        195                 200                 205

Asp Pro Met Ser Lys Asn Arg Cys Gly Leu Pro Gly His Tyr Pro Arg
210                 215                 220

Val Leu Val
225

<210> SEQ ID NO 15
<211> LENGTH: 593
<212> TYPE: PRT
<213> ORGANISM: Mesostigma viride

<400> SEQUENCE: 15

Met Ser Pro Pro Thr Ser Pro Thr Pro Asp Thr Gly His Asp Thr Pro
1               5                   10                  15

Asp Thr Gly His Asp Thr Gly Gly His Gly Ala Val Glu Ile Cys Phe
            20                  25                  30

Ala Pro Cys Glu Glu Asp Cys Val Thr Ile Arg Tyr Phe Val Glu Asn
        35                  40                  45

Asp Phe Glu Gly Cys Ile Pro Gly His Phe Asp Gln Tyr Ser Ser His
50                  55                  60

Gly Ser Leu His Asp Ile Val Lys Ala Ala Leu Tyr Ile Cys Met Val
65                  70                  75                  80

Ile Ser Ile Leu Gln Ile Leu Phe Tyr Gly Phe Gln Trp Trp Arg Lys
                85                  90                  95

Thr Cys Gly Trp Glu Val Trp Phe Val Ala Cys Ile Glu Thr Ser Ile
            100                 105                 110

Tyr Ile Ile Ala Ile Thr Ser Glu Ala Asp Ser Pro Phe Thr Leu Tyr
        115                 120                 125

Leu Thr Asn Gly Gln Ile Ser Pro Gln Leu Arg Tyr Met Glu Trp Leu
        130                 135                 140
```

```
Met Thr Cys Pro Val Ile Leu Ile Ala Leu Ser Asn Ile Thr Gly Met
145                 150                 155                 160

Ala Glu Glu Tyr Asn Lys Arg Thr Met Thr Leu Leu Thr Ser Asp Val
            165                 170                 175

Cys Cys Ile Val Leu Gly Met Met Ser Ala Ala Ser Lys Pro Arg Leu
        180                 185                 190

Lys Gly Ile Leu Tyr Ala Val Gly Trp Ala Phe Gly Ala Trp Thr Tyr
    195                 200                 205

Trp Thr Ala Leu Gln Val Tyr Arg Asp Ala His Lys Ala Val Pro Lys
210                 215                 220

Pro Leu Ala Trp Tyr Val Arg Ala Met Gly Tyr Val Phe Phe Thr Ser
225                 230                 235                 240

Trp Leu Thr Phe Pro Gly Trp Phe Leu Leu Gly Pro Glu Gly Leu Glu
            245                 250                 255

Val Val Thr Gly Thr Val Ser Thr Leu Met His Ala Cys Ser Asp Leu
        260                 265                 270

Ile Ser Lys Asn Leu Trp Gly Phe Met Asp Trp His Leu Arg Val Leu
    275                 280                 285

Val Ala Arg His His Arg Lys Leu Phe Lys Ala Glu Glu His Ala
290                 295                 300

Leu Lys Lys Gly Gln Thr Leu Glu Pro Gly Met Pro Arg Ser Thr Ser
305                 310                 315                 320

Phe Val Arg Gly Leu Gly Asp Asp Val Glu Ile Asp Pro Ser Tyr Glu
            325                 330                 335

Leu Tyr Arg Leu Lys Arg Gln Asn His Pro Glu Tyr Phe Leu Ser Pro
            340                 345                 350

Ala Gln Thr Pro Arg Arg Gly Pro Ser Phe Asp Lys Arg Thr Ser Phe
            355                 360                 365

Glu Met Asp Gly Gly Lys Asn Gly Met Leu Gln Met Met Pro Val Thr
370                 375                 380

Gly Met Gly Met Gly Met Gly Met Gly Met Gly Gly Lys Thr Val
385                 390                 395                 400

Leu Phe Leu Asp Tyr Thr Gly Gly Tyr Val Ser Phe Phe Glu Gln
            405                 410                 415

Gln Leu Ser Asn Met Gly Val Asn Val Thr Lys Cys Trp Ser Asp Asp
            420                 425                 430

Asp Met Tyr Asn Thr Ala Gly Val Ala Asn Val Lys Gln Leu Phe His
            435                 440                 445

Phe Ala Met Ile Pro Asn Asn Ala Leu Gly Gly Gln Met Val Met Asp
            450                 455                 460

Leu Arg Gly Thr Gly Leu Leu Val Ala Tyr Gly Pro Glu Pro Pro
465                 470                 475                 480

Met Pro Gly Met Gly Gln Asp Glu Phe Val Pro Leu Gln Met Pro Gly
            485                 490                 495

Val Pro Tyr Asp Glu Ser Ile Leu His Asn Leu Val Met Arg His Ala
            500                 505                 510

Ile Thr Gln Gly Leu Gly Met Asn Gly Met Gln Gly Asn Met Gly Gln
            515                 520                 525

Gln Gln Gln Met Met Gly Met Gln Gly Asn Met Asn Gly Met Gln Gly
            530                 535                 540

Asn Met Asn Gly Met Gln Gly Asn Met Asn Gly Met Gln Gly Asn Met
545                 550                 555                 560
```

```
Ser Gly Met Gln Gly Asn Met Asn Gly Met Gln Asn Ser Gly Met
                565                 570                 575

Asn Gln Gly Trp Asn Asn Gln Gly Phe Thr Asn Thr Gly Ala Phe Gly
            580                 585                 590

Tyr

<210> SEQ ID NO 16
<211> LENGTH: 737
<212> TYPE: PRT
<213> ORGANISM: Chlamydomonas reinhardtii

<400> SEQUENCE: 16

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile Arg Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
290                 295                 300

Glu Ala Gly Ala Val Asn Lys Gly Thr Gly Lys Tyr Ala Ser Arg Glu
305                 310                 315                 320

Ser Phe Leu Val Met Arg Asp Lys Met Lys Glu Lys Gly Ile Asp Val
                325                 330                 335
```

-continued

```
Arg Ala Ser Leu Asp Asn Ser Lys Glu Val Glu Gln Glu Gln Ala Ala
                340                 345                 350
Arg Ala Ala Met Met Met Met Asn Gly Asn Gly Met Gly Met Gly Met
            355                 360                 365
Gly Met Asn Gly Met Asn Gly Met Gly Gly Met Asn Gly Met Ala Gly
        370                 375                 380
Gly Ala Lys Pro Gly Leu Glu Leu Thr Pro Gln Leu Gln Pro Gly Arg
385                 390                 395                 400
Val Ile Leu Ala Val Pro Asp Ile Ser Met Val Asp Phe Phe Arg Glu
                405                 410                 415
Gln Phe Ala Gln Leu Ser Val Thr Tyr Glu Leu Val Pro Ala Leu Gly
            420                 425                 430
Ala Asp Asn Thr Leu Ala Leu Val Thr Gln Ala Gln Asn Leu Gly Gly
        435                 440                 445
Val Asp Phe Val Leu Ile His Pro Glu Phe Leu Arg Asp Arg Ser Ser
    450                 455                 460
Thr Ser Ile Leu Ser Arg Leu Arg Gly Ala Gly Gln Arg Val Ala Ala
465                 470                 475                 480
Phe Gly Trp Ala Gln Leu Gly Pro Met Arg Asp Leu Ile Glu Ser Ala
                485                 490                 495
Asn Leu Asp Gly Trp Leu Glu Gly Pro Ser Phe Gly Gln Gly Ile Leu
            500                 505                 510
Pro Ala His Ile Val Ala Leu Val Ala Lys Met Gln Gln Met Arg Lys
        515                 520                 525
Met Gln Gln Met Gln Gln Ile Gly Met Met Thr Gly Gly Met Asn Gly
    530                 535                 540
Met Gly Gly Gly Met Gly Gly Met Asn Gly Met Gly Gly Asn
545                 550                 555                 560
Gly Met Asn Asn Met Gly Asn Gly Met Gly Gly Met Gly Asn Gly
                565                 570                 575
Met Gly Gly Asn Gly Met Asn Gly Met Gly Gly Asn Gly Met Asn
            580                 585                 590
Asn Met Gly Gly Asn Gly Met Ala Gly Asn Gly Met Gly Gly Met
        595                 600                 605
Gly Gly Asn Gly Met Gly Gly Ser Met Asn Gly Met Ser Ser Gly Val
    610                 615                 620
Val Ala Asn Val Thr Pro Ser Ala Ala Gly Gly Met Gly Gly Met Met
625                 630                 635                 640
Asn Gly Gly Met Ala Ala Pro Gln Ser Pro Gly Met Asn Gly Gly Arg
                645                 650                 655
Leu Gly Thr Asn Pro Leu Phe Asn Ala Ala Pro Ser Pro Leu Ser Ser
            660                 665                 670
Gln Leu Gly Ala Glu Ala Gly Met Gly Ser Met Gly Gly Met Gly Gly
        675                 680                 685
Met Ser Gly Met Gly Gly Met Gly Gly Met Gly Gly Met Gly Gly Ala
    690                 695                 700
Gly Ala Ala Thr Thr Gln Ala Ala Gly Gly Asn Ala Glu Ala Glu Met
705                 710                 715                 720
Leu Gln Asn Leu Met Asn Glu Ile Asn Arg Leu Lys Arg Glu Leu Gly
                725                 730                 735
Glu
```

<210> SEQ ID NO 17

```
<211> LENGTH: 355
<212> TYPE: PRT
<213> ORGANISM: Chlamydomonas reinhardtii

<400> SEQUENCE: 17

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
        35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Ile Thr Phe Ala Leu Ser Ala Leu Cys Leu Met Phe Tyr Gly Tyr
            100                 105                 110

Gln Thr Trp Lys Ser Thr Cys Gly Trp Glu Glu Ile Tyr Val Ala Thr
        115                 120                 125

Ile Glu Met Ile Lys Phe Ile Ile Glu Tyr Phe His Glu Phe Asp Glu
    130                 135                 140

Pro Ala Val Ile Tyr Ser Ser Asn Gly Asn Lys Thr Val Trp Leu Arg
145                 150                 155                 160

Tyr Ala Glu Trp Leu Leu Thr Cys Pro Val Ile Leu Ile His Leu Ser
                165                 170                 175

Asn Leu Thr Gly Leu Ala Asn Asp Tyr Asn Lys Arg Thr Met Gly Leu
            180                 185                 190

Leu Val Ser Asp Ile Gly Thr Ile Val Trp Gly Ala Thr Ser Ala Met
        195                 200                 205

Ala Thr Gly Tyr Val Lys Val Ile Phe Phe Cys Leu Gly Leu Cys Tyr
    210                 215                 220

Gly Ala Asn Thr Phe Phe His Ala Ala Lys Ala Tyr Ile Glu Gly Tyr
225                 230                 235                 240

His Thr Val Pro Lys Gly Arg Cys Arg Gln Val Val Thr Gly Met Ala
                245                 250                 255

Trp Leu Phe Phe Val Ser Trp Gly Met Phe Pro Ile Leu Phe Ile Leu
            260                 265                 270

Gly Pro Glu Gly Phe Gly Val Leu Ser Val Tyr Gly Ser Thr Val Gly
        275                 280                 285

His Thr Ile Ile Asp Leu Met Ser Lys Asn Cys Trp Gly Leu Leu Gly
    290                 295                 300

His Tyr Leu Arg Val Leu Ile His Glu His Ile Leu Ile His Gly Asp
305                 310                 315                 320

Ile Arg Lys Thr Thr Lys Leu Asn Ile Gly Gly Thr Glu Ile Glu Val
                325                 330                 335

Glu Thr Leu Val Glu Asp Glu Ala Glu Ala Gly Ala Val Ala Pro Ser
            340                 345                 350

Pro Pro Leu
        355

<210> SEQ ID NO 18
<211> LENGTH: 359
<212> TYPE: PRT
```

<213> ORGANISM: Chlamydomonas reinhardtii

<400> SEQUENCE: 18

```
Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
        35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Ile Thr Phe Ala Leu Ser Ala Leu Cys Leu Met Phe Tyr Gly Tyr
            100                 105                 110

Gln Thr Trp Lys Ser Thr Cys Gly Trp Glu Glu Ile Tyr Val Ala Thr
        115                 120                 125

Ile Glu Met Ile Lys Phe Ile Ile Glu Tyr Phe His Glu Phe Asp Glu
130                 135                 140

Pro Ala Val Ile Tyr Ser Ser Asn Gly Asn Lys Thr Val Trp Leu Arg
145                 150                 155                 160

Tyr Ala Glu Trp Leu Leu Thr Cys Pro Val Ile Leu Ile His Leu Ser
                165                 170                 175

Asn Leu Thr Gly Leu Ala Asn Asp Tyr Asn Lys Arg Thr Met Gly Leu
            180                 185                 190

Leu Val Ser Asp Ile Gly Thr Ile Val Trp Gly Thr Thr Ala Ala Leu
        195                 200                 205

Ser Lys Gly Tyr Val Arg Val Ile Phe Phe Leu Met Gly Leu Cys Tyr
210                 215                 220

Gly Ile Tyr Thr Phe Phe Asn Ala Ala Lys Val Tyr Ile Glu Ala Tyr
225                 230                 235                 240

His Thr Val Pro Lys Gly Arg Cys Arg Gln Val Val Thr Gly Met Ala
                245                 250                 255

Trp Leu Phe Phe Val Ser Trp Gly Met Phe Pro Ile Leu Phe Ile Leu
            260                 265                 270

Gly Pro Glu Gly Phe Gly Val Leu Ser Val Tyr Gly Ser Thr Val Gly
        275                 280                 285

His Thr Ile Ile Asp Leu Met Ser Lys Asn Cys Trp Gly Leu Leu Gly
290                 295                 300

His Tyr Leu Arg Val Leu Ile His Glu His Ile Leu Ile His Gly Asp
305                 310                 315                 320

Ile Arg Lys Thr Thr Lys Leu Asn Ile Gly Gly Thr Glu Ile Glu Val
                325                 330                 335

Glu Thr Leu Val Glu Asp Glu Ala Glu Ala Gly Ala Val Asn Lys Gly
            340                 345                 350

Thr Gly Lys Tyr Glu Ser Ser
        355
```

<210> SEQ ID NO 19
<211> LENGTH: 737
<212> TYPE: PRT
<213> ORGANISM: Chlamydomonas reinhardtii -continued

<400> SEQUENCE: 19

```
Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Asn Lys Gly Thr Gly Lys Tyr Ala Ser Arg Glu
305                 310                 315                 320

Ser Phe Leu Val Met Arg Asp Lys Met Lys Glu Lys Gly Ile Asp Val
                325                 330                 335

Arg Ala Ser Leu Asp Asn Ser Lys Glu Val Glu Gln Glu Gln Ala Ala
            340                 345                 350

Arg Ala Ala Met Met Met Met Asn Gly Asn Gly Met Gly Met Gly Met
        355                 360                 365

Gly Met Asn Gly Met Asn Gly Met Gly Gly Met Asn Gly Met Ala Gly
    370                 375                 380

Gly Ala Lys Pro Gly Leu Glu Leu Thr Pro Gln Leu Gln Pro Gly Arg
385                 390                 395                 400

Val Ile Leu Ala Val Pro Asp Ile Ser Met Val Asp Phe Phe Arg Glu
                405                 410                 415
```

Gln Phe Ala Gln Leu Ser Val Thr Tyr Glu Leu Val Pro Ala Leu Gly
                420                 425                 430

Ala Asp Asn Thr Leu Ala Leu Val Thr Gln Ala Gln Asn Leu Gly Gly
            435                 440                 445

Val Asp Phe Val Leu Ile His Pro Glu Phe Leu Arg Asp Arg Ser Ser
450                 455                 460

Thr Ser Ile Leu Ser Arg Leu Arg Gly Ala Gly Gln Arg Val Ala Ala
465                 470                 475                 480

Phe Gly Trp Ala Gln Leu Gly Pro Met Arg Asp Leu Ile Glu Ser Ala
                485                 490                 495

Asn Leu Asp Gly Trp Leu Glu Gly Pro Ser Phe Gly Gln Gly Ile Leu
            500                 505                 510

Pro Ala His Ile Val Ala Leu Val Ala Lys Met Gln Gln Met Arg Lys
        515                 520                 525

Met Gln Gln Met Gln Gln Ile Gly Met Met Thr Gly Gly Met Asn Gly
530                 535                 540

Met Gly Gly Gly Met Gly Gly Gly Met Asn Gly Met Gly Gly Gly Asn
545                 550                 555                 560

Gly Met Asn Asn Met Gly Asn Gly Met Gly Gly Gly Met Gly Asn Gly
                565                 570                 575

Met Gly Gly Asn Gly Met Asn Gly Met Gly Gly Asn Gly Met Gly Asn
            580                 585                 590

Asn Met Gly Gly Asn Gly Met Ala Gly Asn Gly Met Gly Gly Gly Met
        595                 600                 605

Gly Gly Asn Gly Met Gly Gly Ser Met Asn Gly Met Gly Ser Ser Gly Val
                610                 615                 620

Val Ala Asn Val Thr Pro Ser Ala Ala Gly Met Gly Gly Met Met
625                 630                 635                 640

Asn Gly Gly Met Ala Ala Pro Gln Ser Pro Gly Met Asn Gly Gly Arg
                645                 650                 655

Leu Gly Thr Asn Pro Leu Phe Asn Ala Ala Pro Ser Pro Leu Ser Ser
            660                 665                 670

Gln Leu Gly Ala Glu Ala Gly Met Gly Ser Met Gly Gly Met Gly Gly
        675                 680                 685

Met Ser Gly Met Gly Gly Met Gly Gly Met Gly Gly Met Gly Gly Ala
690                 695                 700

Gly Ala Ala Thr Thr Gln Ala Ala Gly Gly Asn Ala Glu Ala Glu Met
705                 710                 715                 720

Leu Gln Asn Leu Met Asn Glu Ile Asn Arg Leu Lys Arg Glu Leu Gly
                725                 730                 735

Glu

<210> SEQ ID NO 20
<211> LENGTH: 350
<212> TYPE: PRT
<213> ORGANISM: Chlamydomonas reinhardtii

<400> SEQUENCE: 20

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
        35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Phe Ala Leu Ser Val Ala Cys Leu Gly Trp Tyr Ala Tyr
                100                 105                 110

Gln Ala Trp Arg Ala Thr Cys Gly Trp Glu Glu Val Tyr Val Ala Leu
                115                 120                 125

Ile Glu Met Met Lys Ser Ile Ile Glu Ala Phe His Glu Phe Asp Ser
    130                 135                 140

Pro Ala Thr Leu Trp Leu Ser Ser Gly Asn Gly Val Val Trp Met Arg
145                 150                 155                 160

Tyr Gly Glu Trp Leu Leu Thr Cys Pro Val Leu Leu Ile His Leu Ser
                165                 170                 175

Asn Leu Thr Gly Leu Lys Asp Asp Tyr Ser Lys Arg Thr Met Gly Leu
                180                 185                 190

Leu Val Ser Asp Val Gly Cys Ile Val Trp Gly Ala Thr Ser Ala Met
    195                 200                 205

Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
                260                 265                 270

Gly Pro Glu Gly Phe Gly His Ile Ser Pro Tyr Gly Ser Ala Ile Gly
    275                 280                 285

His Ser Ile Leu Asp Leu Ile Ala Lys Asn Met Trp Gly Val Leu Gly
    290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser
                340                 345                 350

<210> SEQ ID NO 21
<211> LENGTH: 350
<212> TYPE: PRT
<213> ORGANISM: Chlamydomonas reinhardtii

<400> SEQUENCE: 21

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
                20                  25                  30

Pro Val Ala Thr Gln Asp Gly Pro Asp Tyr Val Phe His Arg Ala His
            35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu

```
              65                  70                  75                  80
Lys Ser Asn Gly Thr Asn Ala Glu Lys Leu Ala Ala Asn Ile Leu Gln
                        85                  90                  95

Trp Val Val Phe Ala Leu Ser Val Ala Cys Leu Gly Trp Tyr Ala Tyr
                    100                 105                 110

Gln Ala Trp Arg Ala Thr Cys Gly Trp Glu Val Tyr Val Ala Leu
                115                 120                 125

Ile Glu Met Met Lys Ser Ile Ile Glu Ala Phe His Glu Phe Asp Ser
            130                 135                 140

Pro Ala Thr Leu Trp Leu Ser Ser Gly Asn Gly Val Val Trp Met Arg
145                 150                 155                 160

Tyr Gly Glu Trp Leu Leu Thr Cys Pro Val Ile Leu Ile His Leu Ser
                    165                 170                 175

Asn Leu Thr Gly Leu Lys Asp Asp Tyr Ser Lys Arg Thr Met Gly Leu
                180                 185                 190

Leu Val Ser Asp Val Gly Cys Ile Val Trp Gly Ala Thr Ser Ala Met
            195                 200                 205

Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
                260                 265                 270

Gly Pro Glu Gly Phe Gly His Ile Ser Pro Tyr Gly Ser Ala Ile Gly
                275                 280                 285

His Ser Ile Leu Asp Leu Ile Ala Lys Asn Met Trp Gly Val Leu Gly
            290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser
            340                 345                 350

<210> SEQ ID NO 22
<211> LENGTH: 350
<212> TYPE: PRT
<213> ORGANISM: Chlamydomonas reinhardtii

<400> SEQUENCE: 22

Met Val Ser Arg Arg Pro Trp Leu Leu Ala Leu Ala Leu Ala Val Ala
1                5                  10                  15

Leu Ala Ala Gly Ser Ala Gly Ala Ser Thr Gly Ser Asp Ala Thr Val
                20                  25                  30

Pro Val Ala Thr Gln Asp Gly Pro Asp Tyr Val Phe His Arg Ala His
            35                  40                  45

Glu Arg Met Leu Phe Gln Thr Ser Tyr Thr Leu Glu Asn Asn Gly Ser
        50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                    85                  90                  95
```

```
Trp Val Val Phe Ala Leu Ser Val Ala Cys Leu Gly Trp Tyr Ala Tyr
                100                 105                 110

Gln Ala Trp Arg Ala Thr Cys Gly Trp Glu Glu Val Tyr Val Ala Leu
            115                 120                 125

Ile Glu Met Met Lys Ser Ile Ile Glu Ala Phe His Glu Phe Asp Ser
        130                 135                 140

Pro Ala Thr Leu Trp Leu Ser Ser Gly Asn Gly Val Val Trp Met Arg
145                 150                 155                 160

Tyr Gly Glu Trp Leu Leu Thr Cys Pro Val Leu Leu Ile His Leu Ser
                165                 170                 175

Asn Leu Thr Gly Leu Lys Asp Asp Tyr Ser Lys Arg Thr Met Gly Leu
            180                 185                 190

Leu Val Ser Asp Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Pro Tyr Gly Ser Ala Ile Gly
        275                 280                 285

His Ser Ile Leu Asp Leu Ile Ala Lys Asn Met Trp Gly Val Leu Gly
290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser
            340                 345                 350

<210> SEQ ID NO 23
<211> LENGTH: 350
<212> TYPE: PRT
<213> ORGANISM: Chlamydomonas reinhardtii

<400> SEQUENCE: 23

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
        35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Val Phe Ala Leu Ser Val Ala Cys Leu Gly Trp Tyr Ala Tyr
                100                 105                 110

Gln Ala Trp Arg Ala Thr Cys Gly Trp Glu Glu Val Tyr Val Ala Leu
            115                 120                 125
```

```
Ile Glu Met Met Lys Ser Ile Ile Glu Ala Phe His Glu Phe Asp Ser
130                 135                 140

Pro Ala Thr Leu Trp Leu Ser Ser Gly Asn Gly Val Val Trp Met Arg
145                 150                 155                 160

Tyr Gly Glu Trp Leu Leu Thr Cys Pro Val Ile Leu Ile His Leu Ser
                165                 170                 175

Asn Leu Thr Gly Leu Lys Asp Asp Tyr Ser Lys Arg Thr Met Gly Leu
                180                 185                 190

Leu Val Ser Asp Val Gly Cys Ile Val Trp Gly Ala Thr Ser Ala Met
            195                 200                 205

Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
                260                 265                 270

Gly Pro Glu Gly Phe Gly His Ile Ser Pro Tyr Gly Ser Ala Ile Gly
            275                 280                 285

His Ser Ile Leu Asp Leu Ile Ala Lys Asn Met Trp Gly Val Leu Gly
290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Glu Asp Lys Tyr Glu Ser Ser
                340                 345                 350

<210> SEQ ID NO 24
<211> LENGTH: 357
<212> TYPE: PRT
<213> ORGANISM: Artificial Sequence
<220> FEATURE:
<223> OTHER INFORMATION: Synthetic construct

<400> SEQUENCE: 24

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
        50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
                100                 105                 110

Thr Trp Lys Ser Thr Cys Gly Trp Glu Glu Ile Tyr Val Ala Thr Ile
            115                 120                 125

Glu Met Ile Lys Phe Ile Ile Glu Tyr Phe His Glu Phe Asp Glu Pro
130                 135                 140
```

```
Ala Thr Leu Trp Leu Ser Ser Gly Asn Gly Val Val Trp Met Arg Tyr
145                 150                 155                 160

Gly Thr Trp Leu Leu Thr Cys Pro Val Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Ile Ala Cys Ile Val Trp Gly Ala Thr Ser Ala Met Cys
            195                 200                 205

Thr Gly Trp Thr Lys Ile Leu Phe Phe Leu Ile Ser Leu Ser Tyr Gly
        210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
        290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Asp Asp Thr Val Lys Gln Ser Thr Ala
            340                 345                 350

Lys Tyr Ala Ser Arg
        355

<210> SEQ ID NO 25
<211> LENGTH: 344
<212> TYPE: PRT
<213> ORGANISM: Artificial Sequence
<220> FEATURE:
<223> OTHER INFORMATION: Synthetic construct

<400> SEQUENCE: 25

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
130                 135                 140
```

```
Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
            195                 200                 205

Thr Gly Trp Thr Lys Ile Leu Phe Phe Leu Ile Ser Leu Ser Tyr Gly
        210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
                260                 265                 270

Thr Glu Gly Phe Gly His Ile Ser Pro Tyr Gly Ser Ala Ile Gly His
            275                 280                 285

Ser Ile Leu Asp Leu Ile Ala Lys Asn Met Trp Gly Val Leu Gly Asn
        290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 26
<211> LENGTH: 69
<212> TYPE: DNA
<213> ORGANISM: Homo sapiens

<400> SEQUENCE: 26
gccaccatgc attggggaac cctgtgcgga ttcttgtggc tttggcccta tcttttctat    60
gtccaagct                                                            69

<210> SEQ ID NO 27
<211> LENGTH: 96
<212> TYPE: DNA
<213> ORGANISM: Homo sapiens

<400> SEQUENCE: 27
tttgtgaacc aacacctgtg cggctcacac ctggtggaag ctctctacct agtgtgcggg    60
gaacgaggct tcttctacac accccgtacc aagcgg                              96

<210> SEQ ID NO 28
<211> LENGTH: 99
<212> TYPE: DNA
<213> ORGANISM: Homo sapiens

<400> SEQUENCE: 28
gaggcagagg acctgcaggt ggggcaggtg gagctgggcg ggggccctgg tgcaggcagc    60
ctgcagccct ggccctgga ggggtcccgt cagaagcgt                            99

<210> SEQ ID NO 29
<211> LENGTH: 63
```

```
<212> TYPE: DNA
<213> ORGANISM: Homo sapiens

<400> SEQUENCE: 29
ggcattgtgg aacaatgctg taccagcatc tgctccctct accagctgga gaactactgc      60
aac                                                                    63
```

BIOENGINEERED ADIPOCYTES FOR THE LIGHT-CONTROLLED RELEASE OF INSULIN AND OTHER PEPTIDES

CROSS-REFERENCE TO RELATED APPLICATIONS

This application is a National Entry Application of PCT application no PCT/CA2015/05150 filed on Nov. 6, 2015, and published in English under PCT Article 21(2), which itself claims the benefits of U.S. provisional application Ser. No. 62/076,599 filed Nov. 7, 2014. The content of all documents above is incorporated herein by reference.

SEQUENCE LISTING

This application contains a Sequence Listing in computer readable form entitled "15949_9_SeqList.txt", created Nov. 6, 2015 and having a size of about 82 KB. The computer readable form is incorporated herein by reference.

TECHNICAL FIELD

The present invention generally relates to the controlled release of polypeptides from adipocytes.

BACKGROUND ART

As of 2013, over 3 million Canadians live with diabetes. Type I diabetes (T1D) accounts for approximately 10% of these cases and is characterized by uncontrolled fluctuations in blood glucose resulting from the destruction of insulin-secreting beta-cells in the islets of the pancreas.

Expression and secretion of mature insulin necessary to regulate blood glucose levels is confined to the beta-cells in pancreatic islets. In T1D, an inappropriate autoimmune response leads to beta-cell destruction, absolute insulin insufficiency and overt diabetes. Currently, insulin replacement therapy and diet/lifestyle control has been the mainstay treatment for T1D but is not a cure.

There is thus a need for novel approaches for the controlled delivery of bioactive polypeptides, such as insulin, and for novel therapeutic strategies for the treatment of conditions that can benefit from the controlled delivery of such peptides, such as T1D.

The present description refers to a number of documents, the content of which is herein incorporated by reference in their entirety.

SUMMARY OF THE INVENTION

The present invention generally relates to the controlled release of polypeptides from adipocytes, and in aspects relates to various products, methods and uses for the controlled release of polypeptides from adipocytes.

In aspects and embodiments, the present invention relates to the following items 1 to 46:
1. An engineered adipocyte comprising:
  a channelrhodopsin (ChR) polypeptide; and
  a secretory polypeptide precursor comprising a bioactive polypeptide and a signal peptide suitable for secretion of said bioactive polypeptide by said engineered adipocyte.
2. The engineered adipocyte of item 1, wherein said secretory polypeptide precursor is a prohormone or preprohormone.
3. The engineered adipocyte of item 1 or 2, wherein said secretory polypeptide precursor is not naturally produced by a native adipocyte.
4. The engineered adipocyte of item 2 or 3, wherein said preprohormone is preproinsulin and said bioactive polypeptide is insulin, and wherein said preproinsulin comprises one or more recognition sequences for one or more proteases expressed by said engineered adipocyte.
5. The engineered adipocyte of item 4, wherein said one or more proteases is furin.
6. The engineered adipocyte of item 5, wherein said one or more recognition sequences comprises the amino acid sequence RXKR (SEQ ID NO: 1), wherein X is any amino acid.
7. The engineered adipocyte of any one of items 1 to 6, wherein said signal peptide comprises a signal peptide from an adipokine.
8. The engineered adipocyte of item 7, wherein said adipokine is human leptin.
9. The engineered adipocyte of item 8, wherein said signal peptide comprises the amino acid sequence MHWGTLCGFLWLWPYLFYQA (SEQ ID NO: 2).
10. The engineered adipocyte of any one of items 1 to 9, wherein said adipocyte is a subcutaneous adipocyte.
11. The engineered adipocyte of any one of items 1 to 10, wherein said ChR polypeptide comprises the amino acid sequence of SEQ ID NO: 10.
12. The engineered adipocyte of any one of items 1 to 11, said engineered adipocyte comprising:
  a first nucleic acid encoding said channelrhodopsin (ChR) polypeptide; and
  a second nucleic acid encoding said secretory polypeptide precursor comprising said bioactive polypeptide and said signal peptide suitable for secretion of said bioactive polypeptide by said engineered adipocyte.
13. The engineered adipocyte of item 12, wherein said first nucleic acid and/or second nucleic acid is/are operably linked to a viral promoter.
14. The engineered adipocyte of item 12 or 13, wherein said first nucleic acid and/or second nucleic acid is/are operably linked to a promoter from a gene naturally expressed by native adipocytes.
15. The engineered adipocyte of any one of items 12 to 14, wherein said first nucleic acid and/or second nucleic acid is/are present in one or more vectors.
16. The engineered adipocyte of item 15, wherein said vector is a viral vector.
17. The engineered adipocyte of item 16, wherein said viral vector is an adenoviral vector, an adeno-associated vector (AAV) or a lentiviral vector.
18. The engineered adipocyte of any one of items 15 to 17, wherein said first nucleic acid and second nucleic acid are present in the same vector.
19. A vector comprising the first nucleic acid and second nucleic acid defined in any one of items 12 to 14.
20. The vector of item 19, wherein said vector is a viral vector.
21. The vector of item 20, wherein said viral vector is an adenoviral vector, an adeno-associated vector (AAV) or a lentiviral vector.
22. A method for inducing the secretion of a bioactive polypeptide by the engineered adipocyte defined in any one of items 1 to 18, said method comprising exposing said engineered adipocyte to a light signal suitable to activate said channelrhodopsin (ChR) polypeptide.
23. The method of item 22, wherein said light signal is a blue light signal.

24. The method of item 23, wherein said blue light signal has a wavelength of between about 460 nm to about 480 nm.

25. The method of item 24, wherein said blue light signal has a wavelength of about 470 nm.

26. Use of the engineered adipocyte defined in any one of items 1 to 18 exposed to a light signal suitable to activate said channelrhodopsin (ChR) polypeptide for inducing the secretion of a bioactive polypeptide.

27. Use of the engineered adipocyte defined in any one of items 1 to 18 and a light source suitable to activate said channelrhodopsin (ChR) polypeptide for inducing the secretion of a bioactive polypeptide.

28. The use of item 26 or 27, wherein said light signal is a blue light signal.

29. The use of item 28, wherein said blue light signal has a wavelength of between about 460 nm to about 480 nm.

30. The use of item 29, wherein said blue light signal has a wavelength of about 470 nm.

31. A method for treating a subject with a bioactive polypeptide, said method comprising administering or transplanting an effective amount of the engineered adipocytes defined in any one of items 1 to 18 and exposing said engineered adipocyte to a light signal suitable to activate said channelrhodopsin (ChR) polypeptide.

32. The method of item 31, wherein said subject suffers from diabetes and said bioactive polypeptide is insulin.

33. The method of item 32, wherein said subject suffers from Type I diabetes (T1D).

34. The method of any one of items 31 to 33, wherein said adipocytes are autologous adipocytes.

35. Use of the engineered adipocyte defined in any one of items 1 to 18 for treating a subject with a bioactive polypeptide, wherein said engineered adipocyte is for use with a light source suitable to activate said channelrhodopsin (ChR) polypeptide.

36. The use of item 35, wherein said subject suffers from diabetes and said bioactive polypeptide is insulin.

37. The use of item 36, wherein said subject suffers from Type I diabetes (T1D).

38. A system for the treatment of diabetes comprising;
a blood glucose monitoring device or system;
the engineered adipocyte defined in any one of items 1 to 18; and
a light source suitable to produce a light signal to activate said channelrhodopsin (ChR) polypeptide.

39. The system of item 38, wherein said light signal is as defined in any one of items 28 to 30.

40. The engineered adipocyte of any one of items 1 to 18, for use in treating a subject with a bioactive polypeptide, wherein said engineered adipocyte is for use with a light source suitable to activate said channelrhodopsin (ChR) polypeptide.

41. The engineered adipocyte for use according to item 40, wherein said subject suffers from diabetes and said bioactive polypeptide is insulin.

42. The engineered adipocyte for use according to item 41, wherein said subject suffers from Type I diabetes (T1D).

43. The engineered adipocyte of any one of items 1 to 18 and a light source suitable to activate said channelrhodopsin (ChR) polypeptide, for use in treating a subject with a bioactive polypeptide.

44. The engineered adipocyte and light source for use according to item 43, wherein said subject suffers from diabetes and said bioactive polypeptide is insulin.

45. The engineered adipocyte and light source for use according to item 44, wherein said subject suffers from Type I diabetes (T1D).

46. A kit for inducing the secretion of a bioactive polypeptide, or for treating a subject with a bioactive polypeptide, the kit comprising one or more of the following:
the engineered adipocyte of any one of items 1 to 18;
one or more vectors described herein, such as one or more vectors (e.g., the vector of any one of items 19 to 21) comprising the first nucleic acid and second nucleic acid defined in any one of items 12 to 14;
a light source suitable to activate a channelrhodopsin (ChR) polypeptide, as described herein; and
instructions for use of the engineered adipocyte or the one or more vectors, in conjunction with the light source, for inducing the secretion of a bioactive polypeptide, or for treating a subject with a bioactive polypeptide.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIG. 1A shows the sequence of the INSfur-ChIEF-mCherry cassette used to generate the INSfur-ChIEF adenoviral vector (SEQ ID NO: 3). The various portions in the INSfur sequence are indicated above the sequence, with the codon modified to introduce the furin sites indicated by "F". The sequence of ChIEF is in italics and the sequence of mCherry is double underlined. The following restriction sites are also shown: NotI (gcggccgc); BsiWI (cgtacg); SpeI (actagt); XhoI (ctcgag); and XbaI (tctaga).

FIG. 6B shows an image of mCherry red fluorescence from rat adipose tissue transduced with the Ad-INS-ChIEF vector demonstrating efficient gene transduction of primary adipocytes as the gene construct contains the mCherry-tagged ChIEF light-activated cation channel.

FIGS. 7A and 7B depict the amino acid sequences of *Chlamydomonas reinhardtii* ChR1 (SEQ ID NO: 8) and ChR2 (SEQ ID NO: 9), respectively.

DISCLOSURE OF INVENTION

Figure 1B:
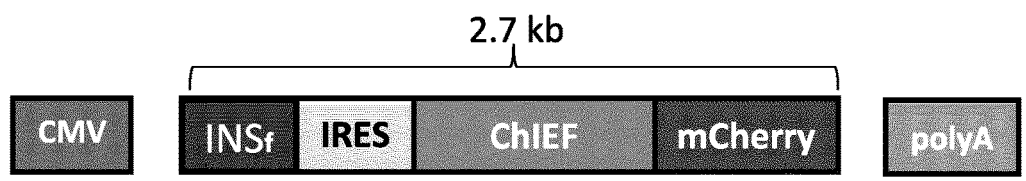
FIG. 1B shows the structure of the INSfur-ChIEF-mCherry cassette used to generate the INSfur-ChIEF adenoviral vector.
Figure 1C:
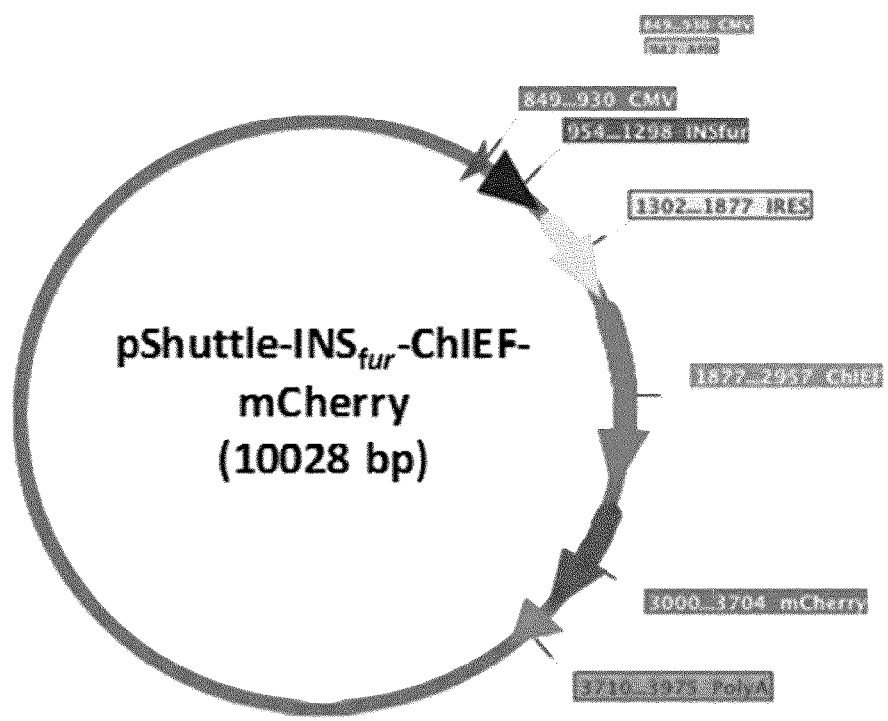
FIG. 1C shows the DNA components of the pShuttle-INSfur-ChIEF-mCherry adenoviral shuttle vector. The DNA was synthesized by Genscript® and inserted into the EcoRV site of pUC57. The 2.7 kb DNA fragment was removed from pUC57 with NotI and XbaI and inserted into the shuttle vector (pShuttle-CMV) between the CMV promoter and the transcription termination site (within the SV40 poly A addition sequence of the vector) after digesting with the same enzymes. An internal ribosome entry site (IRES) element (from encephalomyocarditis Virus, ECMV) was used to permit bicistronic expression of preproinsulin and ChIEF-mCherry from the same viral transcript.
Figure 1D:
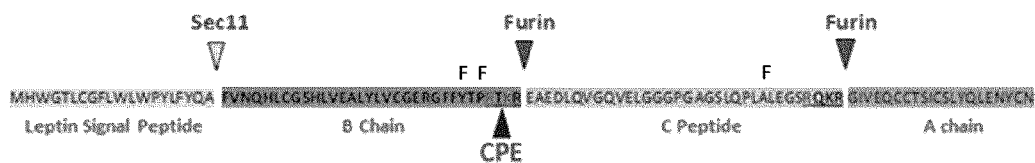
FIG. 1D shows the sequence of the engineered preproinsulin described herein. Upper panel: Amino acid sequence of the designed, modified preproinsulin secretion cassette (SEQ ID NO: 7) that comprises a human leptin signal peptide (SEQ ID NO: 2), followed by an altered human insulin B chain (SEQ ID NO: 4) and C-peptide (SEQ ID NO: 5), and ending with an unmodified A chain (SEQ ID NO: 6). The 3 amino acid mutations introduced to produce the furin sites are indicated by "F". Arrows indicate cleavage sites for furin, signal peptidase (Sec11) and carboxypeptidase E (CPE).
Figure 1E:
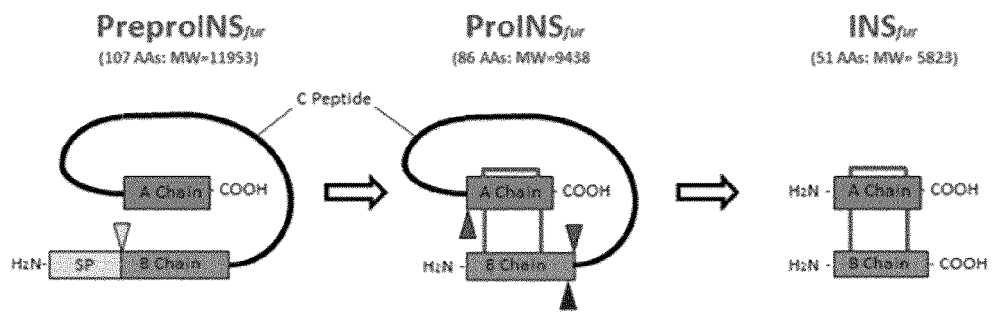
FIG. 1E is a diagram depicting the post-translational processing of the engineered preproinsulin described herein in adipocytes.
Figure 2A:
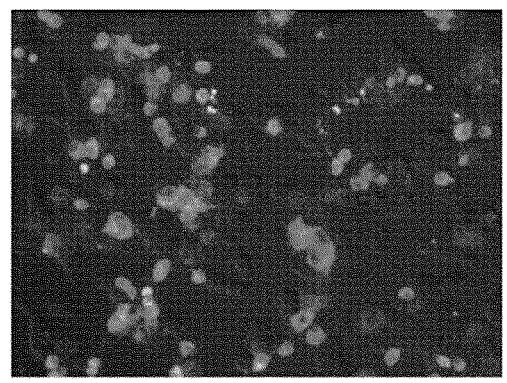
FIG. 2A shows that mCherry is readily detectable by fluorescence microscopy in tSA201 cells transfected with the ChIEF-mCherry fusion construct 24 hours post-transfection.
Figure 2B:
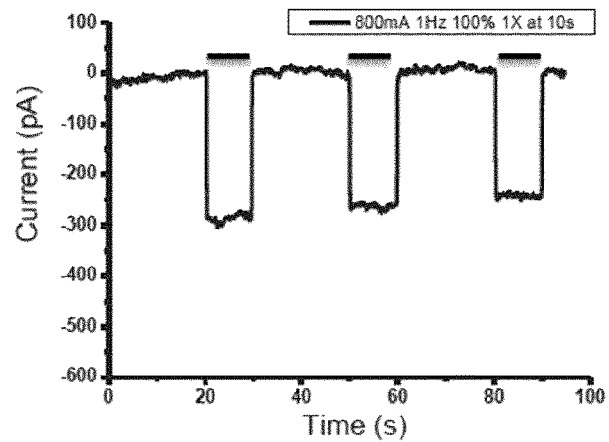
FIG. 2B shows a representative whole-cell recording of light sensitive ChIEF channelrhodopsin current in the transfected tSA201 cells.
Figure 2C:
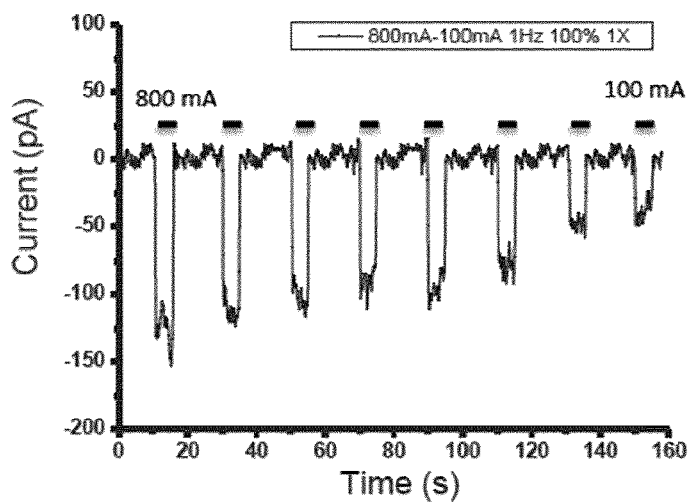
FIG. 2C shows that the inward ChIEF currents in the transfected tSA201 cells are light intensity-dependent.
Figure 2D:
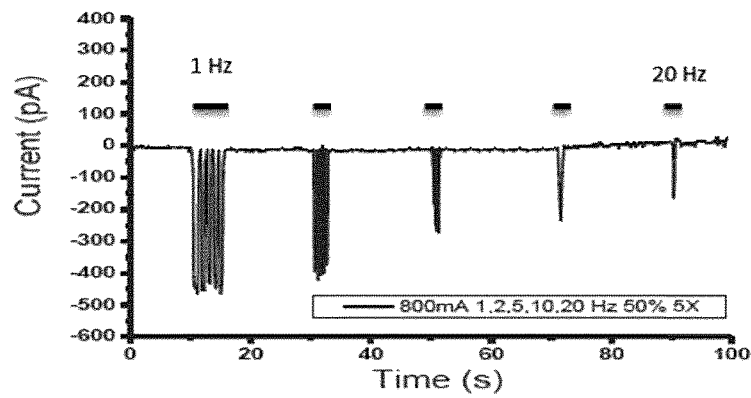
FIG. 2D shows that the inward ChIEF currents in the transfected tSA201 cells are frequency-dependent.
Figure 3:
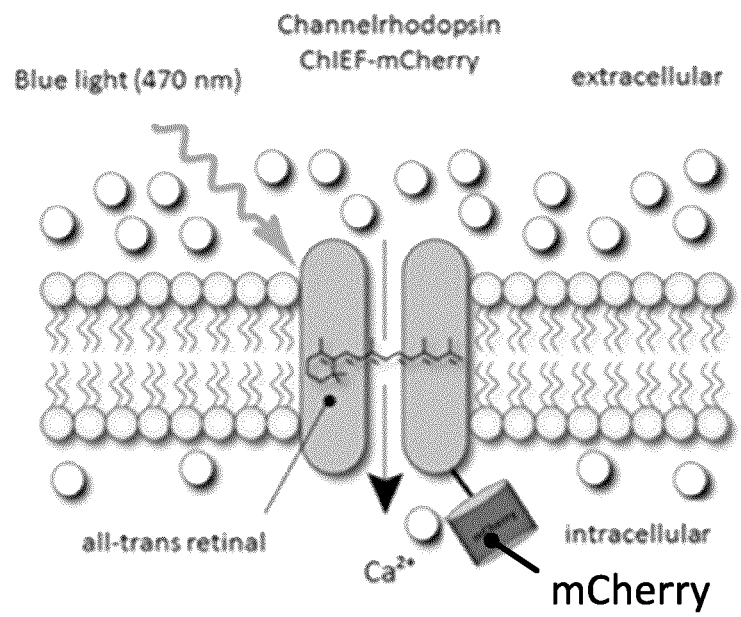
FIG. 3 shows a model depicting the membrane-inserted channelrhodopsin (ChR) fusion protein (ChIEF-mCherry). Exposure to blue light at 470 nm leads to conversion of covalently-bound all-trans retinal to 13-cis retinal that induces a conformational change in the ChR, resulting in the influx of cations such as calcium ions ($Ca^{2+}$).

In the studies described herein, it was found that channelrhodopsin (ChR), which induces cation ($Na^+$, $Ca^{2+}$) influx and has been used for optogenetic control of cell processes in "excitable" cell types, i.e. cells that are known to respond to changes in potential (e.g., neurons, heart cells), may also be used in adipocytes to induce the secretion of a bioactive polypeptide. More specifically, it is demonstrated that engineered adipocytes that express a ChR polypeptide can secrete properly folded insulin in a controlled manner upon exposure to a suitable light source, and that such engineered adipocytes may be grafted (e.g., in a Matrigel® matrix) in mice to regulate blood glucose levels.

Accordingly, in a first aspect, the present invention provides an engineered adipocyte comprising: a light-gated ion channel polypeptide, for example a channelrhodopsin (ChR) polypeptide; and a secretory polypeptide precursor comprising a bioactive polypeptide and a signal peptide suitable for secretion of said bioactive polypeptide by said engineered adipocyte.

In another aspect, the present invention provides an engineered adipocyte comprising: a first nucleic acid encoding a light-gated ion channel polypeptide, for example a channelrhodopsin (ChR) polypeptide; and a second nucleic acid encoding a secretory polypeptide precursor comprising a bioactive polypeptide and a signal peptide suitable for secretion of said bioactive polypeptide by said engineered adipocyte.

The term "adipocyte" is well known in the art to refer to the cells that primarily compose adipose tissue, either the white adipose tissue (WAT, unilocular cells) or brown adipose tissue (BAT, multilocular cells). In an embodiment, the adipocyte is from WAT. In another embodiment, the adipocyte is a subcutaneous adipocyte. In another embodiment, the adipocyte is a human adipocyte.

The term "channelrhodopsin (ChR)" refers to light-gated ion (cation) channels. Channelrhodopsin-1 (ChR1) and Channelrhodopsin-2 (ChR2) from the model organism *Chlamydomonas reinhardtii* were the first discovered channelrhodopsins, and several orthologs and variants have now been discovered and/or engineered. The amino acid sequences of *Chlamydomonas reinhardtii* ChR1 and ChR2 are depicted in FIGS. 7A and 7B, respectively. Although the length of channelrhodopsin proteins varies in nature, it was previously characterized that the N-terminal 200-300 to 400 amino acids, which consist of an N-terminal domain and seven transmembrane helices, are sufficient for normal photocurrent functionality. Accordingly, in some embodiments, a "channelrhodopsin polypeptide" refers to a polypeptide comprising the N-terminal 200-300 to 400 amino acids of a naturally occurring channelrhodopsin protein, chimera, or variant thereof, having photocurrent activity. In some embodiments, a channelrhodopsin polypeptide refers to a polypeptide comprising the N-terminal domain and seven transmembrane domains of one or more naturally occurring channelrhodopsin proteins, a chimera, or variant thereof. Other examples of channelrhodopsin polypeptides include ChR1 and ChR2 from *Volvox carteri* f. *nagariensis* (UniProtKB accession Nos. B4Y103 (SEQ ID NO: 11) and B4Y105 (SEQ ID NO: 12), respectively), ChR1 and ChR2 from *Pleodorina starrii* (UniProtKB accession Nos. H2EZZ5 (SEQ ID NO: 13) and H2EZZ6 (SEQ ID NO: 14), respectively), and ChR1 from *Mesostigma viride* (UniProtKB accession No. F8UVI5, SEQ ID NO: 15).

A number of channelrhodopsin variants are known in the art. For example, Lin et al. (Biophys J, 2009, 96(5): 1803-14) describe making chimeras of the transmembrane domains of ChR1 and ChR2, combined with site-directed mutagenesis. Zhang et al. (Nat Neurosci, 2008, 11(6): 631-3) describe VChR1, which is a red-shifted channelrhodopsin variant. VChR1 has lower light sensitivity and poor membrane trafficking and expression. Other known channelrhodopsin variants include ChR2 (Nagel, G., et al., Proc Natl Acad Sci USA, 2003, 100(24): 13940-5), ChR2/H134R (Nagel, G., et al., Curr Biol, 2005, 15(24): 2279-84, SEQ ID NO: 16), and oChD/oChEF/oChIEF (Lin, J. Y., et al., Biophys J, 2009, 96(5): 1803-14, GenBank accession Nos.: AHA49645.1 (SEQ ID NO: 17), AHA49646.1 (SEQ ID NO: 18) and AHA49647.1 (SEQ ID NO: 10)), which are activated by blue light (470 nm) but show no or less sensitivity to orange/red light. Additional variants have been disclosed by Lin (Lin, J. Y., Experimental Physiology, 2010, 96.1: 19-25), Bamberg et al. (U.S. Pat. No. 8,748,578, GenBank accession No.: AJM13088.1, SEQ ID NO: 19), Hochbaum et al. (Nature Methods 11, 825-833 (2014), that describes a blue-shifted channelrhodopsin called CheRiff. Knopfel et al. (The Journal of Neuroscience, 2010, 30(45): 14998-15004) have reviewed a number of second generation optogenetic tools, including ChR. Current development of channelrhodopsins has produced many variants (e.g., ChR2/H134R, ChETA (E123 mutant), TC, SFO/D156A, oChD, oChEF, oChIEF, CatCh (L132C mutant) and ChRGR) that are maximally activated by blue and green lights (Lin, J. Y. et al., Biophys J 96: 1803-1814 (2009); Wen, L. et al., PLoS One September 23; 5(9) (2010); Kleinlogel, S. et al., Nat Neurosci 14: 513-518 (2011); Nagel, G. et Curr Biol 15: 2279-2284 (2005); Gunaydin, L. A. et al., Nat Neurosci 13: 387-392 (2010); Berndt, A. et al., Nat Neurosci 12: 229-234 (2009); and Berndt, A. et al., Proc Natl Acad Sci USA 108: 7595-7600 (2011), as well as red-shifted channelrhodopsin variants (see, e.g., U.S. Pat. No. 8,759,492, US Patent Publication No. 2013/0066402, GenBank accession No.: AJM30973.1 (SEQ ID NO: 20), AJM30974.1 (SEQ ID NO: 21); Lin et al., Nat. Neurosci. 16(10), 1499-1508 (2013), GenBank accession No. AGT48261.1 (SEQ ID NO: 22) and AGT48260.1 (SEQ ID NO: 23)). Yizhar, O. et al. (Nature 2011, 477(7363):171-8) discloses chimeric channelrhodopsins comprising sequences from *Chlamydomonas reinhradtii* ChR1 and *Volvox carteri* ChR1 designed for improved expression, membrane targeting and functionality in mammalian neural cells (GenBank accession Nos. AEL28923.1 (SEQ ID NO: 24) and AEL28924.1 (SEQ ID NO: 25)). Many of these variants have improved properties regarding the kinetics, expression and level of desensitization. For a tighter control of the expression of the bioactive polypeptide, it may be desirable to use channelrhodopsin variants that are designed to inactivate upon continuous light exposure. Some mutations are known to increase inactivation (Lin, J. Y., et al., Biophys J, 2009, 96(5): 1803-14) or render the channels sensitive to inactivation by yellow light (Berndt, A. et al., Proc Natl Acad Sci USA 108: 7595-7600 (2011); Klapoetke et al., Nature Methods. 2014 11(3):338-46). The use of such variants would advantageously prevent or minimize ambient light-activated bioactive polypeptide (e.g., insulin) secretion unless pulsed light of a suitable wavelength (e.g., blue light of 470 nm) is used.

In an embodiment, the channelrhodopsin comprises a sequence having at least 50, 60, 70, 80, 85, 90, 95, 96, 97, 98 or 99% identity with the amino acid sequence depicted in FIG. 7A (SEQ ID NO: 8) or 7B (SEQ ID NO: 9), or SEQ ID NO: 10, or any one of SEQ ID NOs: 11-25 (and exhibiting light-gated, non-specific cation channel activity), or with the active domain thereof (i.e. the domain responsible for the light-gated, cation channel activity). "Identity" refers to sequence similarity between two polypeptide or nucleic acid molecules (or fragments thereof). Identity can be determined by comparing each position in the aligned sequences. A degree of identity between amino acid or nucleic acid sequences is a function of the number of identical or matching amino acids or nucleotides at positions shared by the sequences. As used herein, a given percentage of identity between sequences denotes the degree of sequence identity in optimally aligned sequences. Optimal alignment of sequences for comparisons of identity may be conducted using a variety of algorithms, such as the local homology algorithm of Smith and Waterman, 1981, Adv. Appl. Math 2: 482, the homology alignment algorithm of Needleman and Wunsch, 1970, J. Mol. Biol. 48: 443, the search for similarity method of Pearson and Lipman, 1988, Proc. Natl. Acad. Sci. USA 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, J. Mol. Biol. 215:403-10 (using the published default settings). Software for performing BLAST analysis may be available through the National Center for Biotechnology Information. The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, Proc. Natl. Acad. Sci. USA 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In an embodiment, the channelrhodopsin is oChIEF (Genbank accession No. AHA49647.1, SEQ ID NO: 10) or an active variant thereof, in a further embodiment the channelrhodopsin is oChIEF (SEQ ID NO: 10).

The channelrhodopsin and variants thereof, and sequences encoding same, are not native to adipocytes.

The term "secretory polypeptide precursor" refers to a polypeptide comprising a bioactive polypeptide and a signal peptide suitable for secretion of the bioactive polypeptide by the engineered adipocytes. A signal peptide (also known as "leader peptide") refers to a short amino acid sequence (typically 5 to 30 amino acids long) present at the N-terminus of a protein and which targets the protein to the secretory pathway. Signal peptide typically comprises a stretch of amino acids that is recognized and cleaved by signal peptidase, thereby releasing the mature polypeptide (e.g., lacking the signal peptide). The signal peptide may be the native signal peptide of the bioactive polypeptide, or another signal peptide which is not native to the bioactive polypeptide, for example a signal peptide from an adipokine (i.e., a cytokine or cell signalling protein naturally secreted by adipocytes) or a hormone naturally secreted by adipocytes. Examples of adipokines or hormones naturally secreted by adipocytes include, for example, leptin, adiponectin, apelin, chemerin, interleukin-6 (IL-6), estradiol, monocyte chemotactic protein-1, plasminogen activator inhibitor-1, retinol binding protein 4, resistin, tumor necrosis factor-alpha (TNFα) and visfatin. In an embodiment, the signal peptide from an adipokines or hormone naturally secreted by adipocytes whose expression and/or secretion is controlled by the intracellular levels of one or more cations. In an embodiment, the signal peptide from an adipokines or hormone naturally secreted by adipocytes whose expression and/or secretion is controlled by the intracellular messenger $Ca^{2+}$, i.e. whose expression and/or secretion is induced upregulated when intracellular $Ca^{2+}$ levels are increased.

In an embodiment, the signal peptide is from human leptin, in a further embodiment it comprises the sequence MHWGTLCGFLWLWPYLFYQA (SEQ ID NO: 2).

The adipocyte may be engineered to express any bioactive polypeptide of interest, for example hormones, cytokines/chemokines, growth hormone, growth factors, clotting factors, enzymes, proteases, etc. The bioactive polypeptide may be a native or naturally-occurring polypeptide, or a variant thereof, or other synthetic bioactive polypeptides. In an embodiment, the secretory polypeptide precursor is not naturally produced/expressed by a native adipocyte. In an embodiment, the bioactive polypeptide of interest is a hormone. Peptide hormones include, for example, amylin, anti-Müllerian hormone, adiponectin, corticotropin, angiotensinogen, vasopressin, atrial-natriuretic peptide, brain natriuretic peptide, calcitonin, cholecystokinin, corticotropin-releasing hormone, cortistatin, enkephalin, endothelin, erythropoietin, follicle-stimulating hormone, galanin, gastric inhibitory polypeptide, gastrin, ghrelin, glucagon, glucagon-like peptide-1, gonadotropin-releasing hormone, growth hormone-releasing hormone, hepcidin, human chorionic gonadotropin, human placental lactogen, growth hormone, inhibin, insulin, insulin-like growth factor, leptin, lipotropin, luteinizing hormone, melanocyte stimulating hormone, motilin, orexin, oxytocin, pancreatic polypeptide, parathyroid hormone, pituitary adenylate cyclase-activating peptide, prolactin, prolactin releasing hormone, relaxin, renin, secretin, somatostatin, thrombopoietin, thyroid-stimulating hormone, thyrotropin-releasing hormone and vasoactive intestinal peptide. In an embodiment, the bioactive polypeptide is insulin or a biologically active variant thereof, in a further embodiment native human insulin. In certain embodiments, for example in cases where the bioactive polypeptide is expressed as a precursor (or immature form) that must be enzymatically processed (e.g., by protease(s)) to generate the mature bioactive polypeptide, the secretory polypeptide precursor may comprises one or more mutations relative to the native sequence to ensure that the precursor is properly processed in the adipocytes (i.e., to insert a sequence recognized and cleaved by a protease expressed by adipocytes). For example, in the case of insulin that is expressed as a precursor (proinsulin) that is normally cleaved by prohormone convertases (PC1/3 and PC2) to yield mature insulin, the PC1/3 and PC2 cleavage sites of the native proinsulin may be replaced by sites optimized for cleavage by a protease which is expressed in adipocytes (contrary to PC1/3 and PC2), such as furin, to allow proper processing of the proinsulin into mature insulin. Other examples of protease expressed by adipocytes include tryptase, elastase and cathepsin K.

In an embodiment, the polypeptide of interest is a therapeutic peptide. The term "therapeutic peptide," as used herein, refers to a peptide comprising two or more amino acids but not more than about 100 amino acids, covalently linked together through one or more amide bonds, wherein upon administration of the peptide (or a precursor thereof) to a subject, the subject receives a therapeutic effect (e.g., administration of the therapeutic peptide treats a cell, or cures, alleviates, relieves or improves a symptom of a disorder). A therapeutic peptide may comprise, e.g., more than two, three, four, five, six, seven, eight, nine, ten, eleven, twelve, thirteen, fourteen, fifteen amino acids. In some embodiments, a therapeutic peptide comprises more than 15, e.g., greater than about 20, 25, 30, 35, 40, 45, 50, 55, 60, 65, 70, 75, 80, 85, or 90 amino acids. For example, in some embodiments, the therapeutic peptide is more than 9, 10, 11 or 12 amino acids in length.

The nucleic acid encoding the ChR polypeptide and the nucleic acid encoding the secretory polypeptide precursor can be operably linked to expression control sequences. The term "expression control sequence" refers to a nucleotide sequence that regulates the transcription or translation of a polynucleotide or the localization of a polypeptide to which to which it is operatively linked. Expression control sequences are "operatively linked" or "operably linked" when the expression control sequence controls or regulates the transcription and, as appropriate, translation of the nucleotide sequence (i.e., a transcription or translation regulatory element, respectively). Thus, an expression control sequence can be a promoter, enhancer, transcription terminator, a start codon (ATG), a splicing signal for intron excision and maintenance of the correct reading frame, a STOP codon, a ribosome binding site, or combinations thereof. In an embodiment, the nucleic acid encoding the ChR polypeptide and the nucleic acid encoding the secretory polypeptide precursor are operably linked to a promoter/enhancer. Any suitable expression control sequence (e.g., promoter, promoter/enhancer) may be used, including viral-based promoters/enhancers (CMV, SV40), "general purpose" promoters that allow gene expression in a wide variety of cell types (e.g., EF1-alpha, CaMKII, or synapsin promoter), or adipocyte-specific promoters/enhancers such as the adiponectin promoter/enhancer (O'Neill et al., Gene Therapy (2014) 21, 653-661; Wang Z V et al., Endocrinology 151:2933-2939) or the adipocyte Protein 2 (aP2) promoter/enhancer (Lee et al., Diabetes, 62: 864-874).

In an embodiment, the nucleic acids are present in one or more vectors. In a further embodiment, the nucleic acid encoding the ChR polypeptide and the nucleic acid encoding the secretory polypeptide precursor are in the same vector, allowing co-expression of the two genes from a single vector (bicistronic). In a further embodiment, the nucleic acid encoding the ChR polypeptide and the nucleic acid encoding the secretory polypeptide precursor are in separate vectors.

Vectors can be introduced into cells (adipocytes) via conventional transformation or transfection techniques. The terms "transformation" and "transfection" refer to techniques for introducing foreign nucleic acid into a host cell, including calcium phosphate or calcium chloride co-precipitation, DEAE-dextran-mediated transfection, lipofection, electroporation, microinjection and viral-mediated transfection (transduction). Suitable methods for transforming or transfecting host cells can for example be found in Sambrook et al. (supra), Sambrook and Russell (supra) and other laboratory manuals.

In an embodiment, the vector is a viral vector, in a further embodiment a viral vector suitable for gene therapy, for example a retroviral vector, a lentiviral vector, or other vectors such as an adenoviral vector or an adeno-associated vector (AAV).

Defective retroviruses are well characterized for use as gene therapy vectors (for a review see Miller, A. D. (1990) Blood 76:271). Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include psiCrip, psiCre, psi2 and psiAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573).

For use as a gene therapy vector, the genome of an adenovirus may be manipulated so that it encodes and expresses the nucleic acid of interest (e.g., a nucleic acid encoding the ChR polypeptide and/or a nucleic acid encoding the secretory polypeptide precursor), but is inactivated in terms of its ability to replicate in a normal lytic viral life cycle. See for example Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992), supra), endothelial cells (Lemarchand et al. (1992) Proc. Natl. Acad. Sci. USA 89:6482-6486), hepatocytes (Herz and Gerard (1993) Proc. Natl. Acad. Sci. USA 90:2812-2816) and muscle cells (Quantin et al. (1992) Proc. Natl. Acad. Sci. USA 89:2581-2584).

Adeno-associated virus (AAV) may be used as a gene therapy vector for delivery of DNA for gene therapy purposes. AAV is a naturally occurring defective virus that requires another virus, such as an adenovirus or a herpes virus, as a helper virus for efficient replication and a productive life cycle (Muzyczka et al. Curr. Topics in Micro. and Immunol. (1992) 158:97-129). AAV may be used to integrate DNA into non-dividing cells (see for example Flotte et al. (1992) Am. J. Respir. Cell. Mol. Biol. 7:349-356; Samulski et al. (1989) J. Virol. 63:3822-3828; and McLaughlin et al. (1989) J. Virol. 62:1963-1973). An AAV vector such as that described in Tratschin et al. (1985) Mol. Cell. Biol. 5: 3251-3260 may be used to introduce DNA into cells (see for example Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J. Virol. 51:611-619; and Flotte et al. (1993) J. Biol. Chem. 268:3781-3790). Lentiviral gene therapy vectors may also be adapted for use in the invention.

In another aspect, the present invention provides a method (in vivo or in vitro) for inducing the secretion of a bioactive polypeptide by the engineered adipocytes defined herein, said method comprising exposing said engineered adipocytes to a light signal (e.g., pulse) suitable to activate said channelrhodopsin (ChR) polypeptide. In another aspect, the present invention provides the use of the engineered adipocytes defined herein for inducing the secretion of a bioactive polypeptide in a biological system, for example in vitro (in a culture medium) or in vivo in a subject. In an embodiment, the engineered adipocytes are exposed or have been exposed to a light signal (e.g., pulse) suitable to activate the channelrhodopsin (ChR) polypeptide.

The light signal can be provided by a light source such as a xenon lamp, a laser, a LED or any other suitable light source. The length, intensity and other parameters of the light signal may be modulated to obtain the desired level of secretion of the bioactive polypeptide. The wavelength of the light signal may be adjusted/adapted to the optimal wavelength at which the expressed ChR polypeptide is activated. In an embodiment, the wavelength of the illuminating light is between about 400 nm and about 600 nm, for example from about 450 nm to about 550 nm, or from about 450 nm to about 490 nm, or from about 460 nm to about 480 nm, for example about 470 nm.

The engineered adipocytes defined herein may be used to induce the secretion, in a controlled manner, of a bioactive polypeptide of interest in a subject in need thereof. Accordingly, in another aspect, the present invention provides a method for treating a subject with a bioactive polypeptide (e.g., for treating a disease using said bioactive polypeptide), said method comprising administering or transplanting an effective amount of the engineered adipocytes defined herein and exposing said engineered adipocytes to a light signal suitable to activate said channelrhodopsin (ChR) polypeptide. In an embodiment, adipocytes are obtained from a subject, engineered to express a ChR polypeptide and a bioactive polypeptide of interest (by introduction of the nucleic acids/vectors defined above), and the engineered adipocytes are reintroduced into the subject (adipocyte graft). This approach may be used for the management/treatment of any disease or condition in which the controlled secretion of a bioactive polypeptide of interest is desirable, for example from the management of hormone deficiencies (or any other protein deficiency). In an embodiment, the subject suffers from diabetes (e.g., type I diabetes), and the bioactive polypeptide expressed by the engineered adipocytes is insulin.

In an embodiment, the subject is a mammal, in a further embodiment a human.

In another aspect, the present invention provides a system for the treatment of diabetes (type I diabetes) comprising;

a blood glucose monitoring device or system (e.g., a blood glucose meter);

the engineered adipocyte defined herein; and a light source suitable to activate said channelrhodopsin (ChR) polypeptide.

In an embodiment, the light source is coupled to the blood glucose monitoring device or system. In such a system, the light source, for example a detachable patch of small blue light emitting LEDs, are placed over the engineered adipocyte graft site, and the blood glucose monitoring device or system is adapted to trigger the light source when the subject's blood glucose levels indicate that the release of insulin is needed. Alternatively, the blood glucose monitoring device or system is used to measure the subject's blood glucose levels, and if based on the levels measured it is determined that the release of insulin is needed, the light source is used to emit a light signal suitable to activate the ChR polypeptide and induce the release of insulin from the engineered adipocytes.

Also provided is a kit or commercial package for inducing the secretion of a bioactive polypeptide, or for treating a subject with a bioactive polypeptide, the kit or commercial package comprising one or more of the following:

(a) an engineered adipocyte as described herein;

(b) one or more vectors described herein, such as one or more vectors comprising a first nucleic acid encoding a channelrhodopsin (ChR) polypeptide as described herein and a second nucleic acid encoding a secretory polypeptide precursor comprising a bioactive polypeptide and a signal peptide as described herein;

(c) a light source suitable to activate a channelrhodopsin (ChR) polypeptide, as described herein; and (d) instructions for use of the engineered adipocyte or the one or more vectors, in conjunction with the light source, for inducing the secretion of a bioactive polypeptide, or for treating a subject with a bioactive polypeptide.

In various embodiments, the kit or commercial package may comprise any combination of the above-noted components. For example, in embodiments, the kit or commercial package may comprise: (a); (a) and (d); (a) and (c); (a), (c) and (d); (b); (b) and (d); (b) and (c); or (b), (c) and (d). The kit or commercial package may further comprise suitable container(s) and optionally other reagents amenable to a method or use described herein. In embodiments, the kit or commercial package may further comprise a blood glucose monitoring device or system as described herein.

MODE(S) FOR CARRYING OUT THE INVENTION

The present invention is illustrated in further details by the following non-limiting examples.

Example 1: Materials and Methods

Construction of pShuttle-INSfur-ChIEF-mCherry (FIGS. 1A to D).

The $INS_{fur}$ cassette encodes a human leptin leader peptide followed by mutated human preproinsulin B-Chain, C-Peptide and A-Chain. Modified triplets that were introduced to encode optimal furin sites (RXKR) are indicated by F in FIG. 1A. The following DNA was synthesized by Genscript® and inserted into pUC57. The LacZ-ChIEF mCherry fragment was liberated from pUC57 with NotI and XbaI and inserted into pShuttle-CMV after cutting with the same enzymes to yield pShuttle-INSfur.

Following processing by Furin (FIG. 1D), the mature insulin secreted has only 1 mutation in its B-chain (L50R) and none in the A-chain (relative to native insulin). The leader peptide is that from human Leptin. NCBI: Leptin: NM_000230.2. The ChIEF sequence here has 2 extra N-terminal amino acids (Thr-Ser) that comprises an in-frame SpeI site (actagt). This was introduced to enable easy replacement of ChIEF with other channelrhodopsins by cut- and paste. mCherry is fused to the C-terminus of ChIEF via an in-frame XhoI site (ctcgag). ChIEF is activated by blue light but shows no sensitivity to red or orange light.

Adipose tissue.

Inguinal white adipose tissue was isolated from Sprague-Dawley male rat (6 months old) and kept in Krebs Ringers Henseilet buffer (50 mM HEPES, 137 mM NaCl, 4.7 mM KCl, 2 mM $CaCl_2$, 1.3 mM $MgSO_4.[7H_2O]$, 5 mM glucose, 4% BSA). The tissue was cut into 100 mg pieces which were subsequently each cut into ~1 mm segments. The tissue pieces were rinsed in 3T3-L1 differentiated media (DMEM with 10% FBS and 1% penicillin-streptomycin) and added to 6 well plates, each well containing 100 mgs of tissue. The tissue was incubated overnight (37° C., 5% $CO_2$) in 3T3-L1 differentiated media. The following day, transduction of the tissue with Ad-INSfur-ChIEF ($10^8$ pfu) or the control Ad-mCherry vector ($10^8$ pfu) was initiated by the addition of the adenoviral constructs mixed with 1 mL of 3T3-L1 differentiated media to respective wells (i.e. "co-culturing" the tissue with the adenoviruses). After transduction, the tissue was kept in the dark (covered in aluminum foil) and only exposed to red light, if necessary. Following overnight incubation (37° C., 5% $CO_2$), the media was changed on all wells. 96 h post transduction, the tissue was used for stimulation with blue light (470 nm) for which the protocol was composed of 20 s blue light (470 nm) exposure (ThorLabs®) followed by 40 s dark. This cycle was repeated 10× for each well for a total of 3.3 min of blue light (470 nm) exposure. Samples (200 µL) of the solution were taken one hour prior to blue light (470 nm) stimulation, after the stimulation, and 1 h after the stimulation. Samples were also concurrently taken from tissue that was not stimulated with blue light. The amount of insulin released in all samples was quantified using the MesaScale® Discovery human insulin assay. Resulting data were graphed and analyzed using GraphPad Prism®.

3T3-L1 Adipocytes.

3T3-L1 preadipocytes were cultured and differentiated using DMEM media with 167 nM insulin+10 uM dexamethasone and 0.5 mM 3-isobutyl-1-methylxanthine with mature 3T3-L1 adipocytes appearing 7 days post-induction of differentiation. Mature 3T3-L1 adipocytes were then transduced with Ad-INSfur-ChIEF or Ad-mCherry (MOI=100) with the addition of 10 µL of poly-L-lysine (using serum-free media). The cells were kept in the dark (covered in aluminum foil) and only exposed to red light for visual inspection. Following a 24 h incubation (37° C., 5% $CO_2$), the media was changed on all dishes. The cells were stimulated with blue light (470 nm) for which the protocol was composed of 20 s blue light (470 nm) exposure followed by 40 s dark (ThorLabs®). This cycle was repeated 10× for each well for a total of 3.3 min of pulsed blue light (470 nm) exposure over 10 min time period. Samples (200 µL) of the solution were taken one hour prior to blue light (470 nm) stimulation, after the stimulation, and 1 h after the stimulation. Samples were also concurrently taken from tissue that was not stimulated with blue light. The amount of insulin released in all samples was quantified using the MesaScale® Discovery human insulin assay.

Primary Rat Adipocytes:

Isolation and Transduction. Subcutaneous white adipose tissue was isolated from the inguinal depot of Sprague-Dawley male rats. Tissue was cleaned and minced into 1 mm³ pieces using two sterile razor blades in Krebs-Ringers Henseleit (KRH) buffer. Tissue was then digested with Type 1 collagenase solution (1 mg/mL in KRH buffer) at 3.5 mL of solution per gram of tissue. Digestion took place in a 37° C. water bath with mild agitation (100 RPM) for 1 hour. Cells were then strained through a 250 µM strainer and the filtered solution was centrifuged at 2500 RPM for 10 min. The supernatant was removed and the cells were re-suspended in 2 mL of DMEM media+10% fetal bovine serum+1% penicillin/streptomycin+167 nM human insulin. The cell suspension (500 µL) was seeded in a T25 cell culture flask and 5 mL of fresh media were added. Cells were incubated at 37° C. in a 5% $CO_2$ incubator. Cells were transduced with AdINSChIEFmCherry or AdmCherry adenovirus (100 MOI). Differentiation into mature adipocytes was induced using 167 nM bovine insulin, 10 µM dexamethasone, and 0.5 mM 3-isobutyl-1-methylxanthine (in DMEM+10% fetal bovine serum+1% penicillin/streptomycin) two days post confluency. Transduction efficiency was monitored using mCherry fluorescence (Texas Red (excitation: 585 nm emission: 624 nm), 60% brightness, EVOS fl) against transmitted light (35% brightness, EVOS fl).

Primary Rat Adipocytes: Blue Light Stimulation Protocol (FIG. 8B).

A 100 µL sample was taken from flask ("24 h basal secretion" sample). Cells were washed 3× with media (DMEM+10% fetal bovine serum+1% penicillin/streptomycin).

At 0 h, 3 mL of media was added, and the cells were incubated at 37° C.

At 0:20 h, a 100 µL sample was taken, and replaced with 100 µL of media ("20 min fresh media" sample).

At 0:30 h, the $1^{st}$ half of the flask was stimulated as follows:

20 s on, 40 s off repeated 10× for a total of 10 min
ThorLabs® light source: M470L2-C1
ThorLabs® driver settings: 1000 mA, 1 Hz, 100% duty cycle, infinite counts.

At 0:40 h, the $2^{nd}$ half of the flask was stimulated (same settings as above).

At 0:50 h, a 100 µL sample was taken, and replaced with 100 µL media ("$1^{st}$ stimulation" sample).

At 1:20 h, a 100 µL sample was taken, and replaced with 100 µL media ("30 min post" sample).

At 1:50 h: a 100 µL sample was taken, and replaced with 100 µL media ("1 h post" sample).

At 2:20 h, cells were stimulated as above

At 2:40 h, a 100 µL sample was taken, and replaced with 100 µL media ("$2^{nd}$ stimulation" sample).

To obtain the "Hourly basal production", the culture media was changed on the cells and then the media was collected after 24 hours in the absence of blue light. Analysis of this media sample generated the "24 h basal secretion" value (see above). To calculate the hourly basal production, the 24 h basal secretion value was divided by 24.

Mice Implanted with Matrigel®-Embedded 3T3 L1 Cells: Preparation of Cells and Grafts.

For AdINSChIEFmCherry-transduction and differentiation of 3T3 L1 cells, 3T3 L1 cells were doubly transduced and differentiated. Briefly, 3T3 L1 were firstly transduced as preadipocytes by incubating AdINSChIEFmCherry or AdmCherry adenovirus (100 MOI) with 0.3 µg/mL poly-L-lysine and OptiMEM® serum-free media on 100 mm treated dishes for 100 min at room temperature. Following this incubation, 3T3 L1 trypsinized cells were plated onto these dishes, and after even distribution, were incubated at 37° C. for another 100 min. After incubation, total volume in dishes was topped off with DMEM media supplemented with 10% bovine calf serum and 1% penicillin/streptomycin. Cells were allowed to become 100% confluent over several days. Two days post confluency, differentiation was initiated by changing media on cells to DMEM supplemented with 10% fetal bovine serum, 1% penicillin/streptomycin, 172 nM bovine insulin, 1 µM dexamethasone, 0.5 mM isobutylmethylxanthine, and 1 µM rosiglitazone (day 0 of differentiation). On day 3 of differentiation, media was changed to DMEM supplemented with 10% fetal bovine serum, 1% penicillin/streptomycin, and 172 nM bovine insulin (differentiated media); cells were maintained in this media hereafter. Four to six days into differentiation, cells were again transduced as per protocol described above onto 35 mm treated dishes, but using differentiated media. Cells were again allowed to become confluent and were again differentiated using protocol described above.

For embedding AdINSChIEFmCherry-transduced, mature 3T3 L1 cells into Matrigel®, cells were washed three times with 1×PBS, then trypsinized with 0.5 mL 0.25% trypsin-EDTA at 37° C. for 7 min, then neutralized with 1.5 mL DMEM media supplemented with 10% fetal bovine serum and 1% penicillin/streptomycin. They were then centrifuged at 1000 RPM for 2 min, resuspended in the same media, and centrifuged again. The supernatant was removed and 200 µL of Matrigel® was added, while keeping everything on ice. The cell-Matrigel® mixture was then allowed to solidify at 37° C. for 15-30 min.

Mice Implanted with Matrigel®-Embedded 3T3 L1 Cells: Implantation of Matrigel®-Embedded AdINSChIEFmCherry-Transduced Mice into Rag1$^{-/-}$ (C57BL/6) Mice.

Male Rag1$^{-/-}$ (C57BL/6) mice were anesthetized with isoflurane and an area of approximately 2×3 cm was shaved on the back. A small incision was made into the skin and the tissue underneath was spread out to create a subcutaneous reserve for the implanted cells. Matrigel®-embedded cells were inserted into the created cavity, and the skin was stapled together. Mice were allowed to recover at least one week prior to experiments.

Image was taken one week after surgery. Lighter areas represent the locations of 3 Matrigel® grafts under the skin of a live mouse as determined by mCherry fluorescence that is expressed in the engineered adipocytes. (Carestream In vivo Fx Pro, excitation: 550 nm, emission: 600 nm).

Mice Implanted with Matrigel®-Embedded 3T3 L1 Cells: Monitoring Blood Glucose Levels in Response to Stimulation with Blue Light.

Mice were fasted 12 hours prior to the experiments. On the day of the experiment, mice were anesthetized with isoflurane, at which point the staples were removed, and a blood glucose measurement was obtained. The mice were then injected with diazoxide (100 mg/kg) to inhibit endogenous pancreatic insulin secretion. One-hour post diazoxide injection, if blood glucose was not sufficiently elevated (0 min), an IP glucose injection was given. Blood glucose was measured every 15 min up to a maximum of two hours. At 30 min and 60 min, blue light was pulsed on the area containing the implants (5 sec on, 5 sec off for total of 10 min; 1000 mA, 8.47 mW).

Example 2: Results tSA201 cells (human embryonal kidney, SV40 transformed, cell line) were transfected with the ChR variant ChIEF C-terminally fused to mCherry (FIGS. 2A to 2D and 3). ChIEF has been chosen over the native ChR1 for its enhanced light-sensitivity and activation properties[12]. mCherry positive cells were subjected to pulses of blue light (470 nm) stimulation and they generated robust inward currents that were dependent on the duration (FIG. 2C) and intensity (FIG. 2D) of light exposure.

Figure 4A:
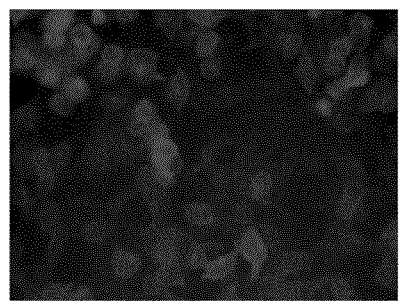
FIG. 4A shows the detection of mCherry by fluorescence microscopy in tSA201 cells transduced with the Ad-INS-ChIEF construct.
Figure 4B:
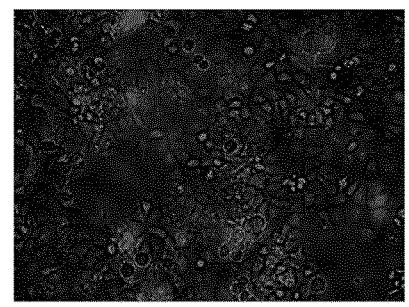
FIG. 4B shows the detection of mCherry by fluorescence microscopy in COS-7 cells transduced with the Ad-INS-ChIEF construct.
Figure 4C:
FIG. 4C shows the detection of mCherry by fluorescence microscopy in 3T3-L1 adipocytes transduced with the Ad-INS-ChIEF construct.
Figure 5A:
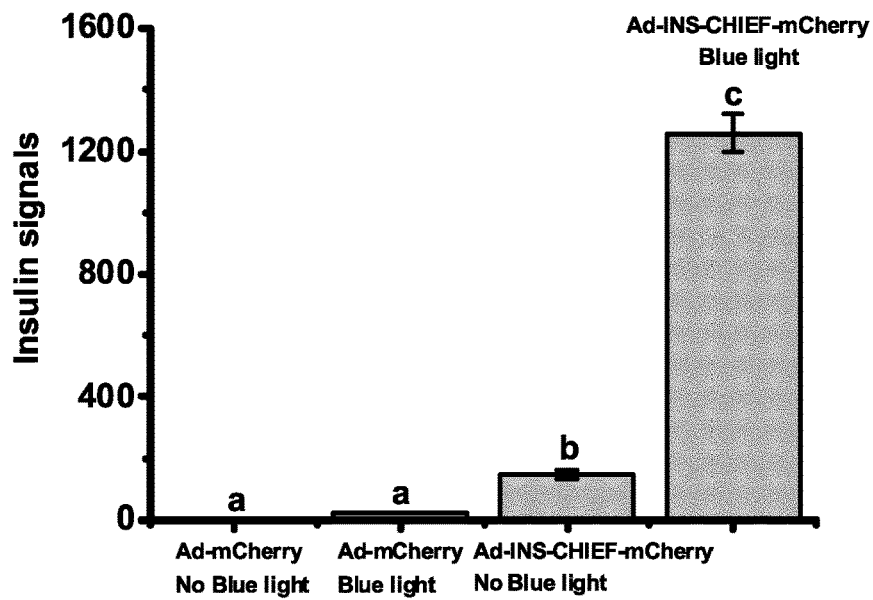
FIGS. 5A and 5B show that differentiated 3T3-L1 adipocytes transduced with the Ad-INS-ChIEF construct secrete insulin when stimulated with blue light under two different conditions.
Figure 5B:
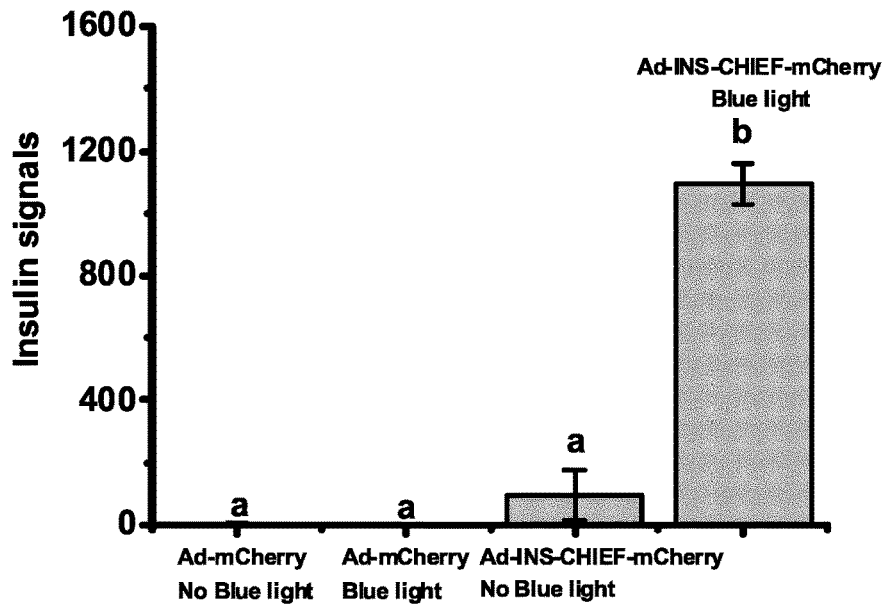
Figure 6A:
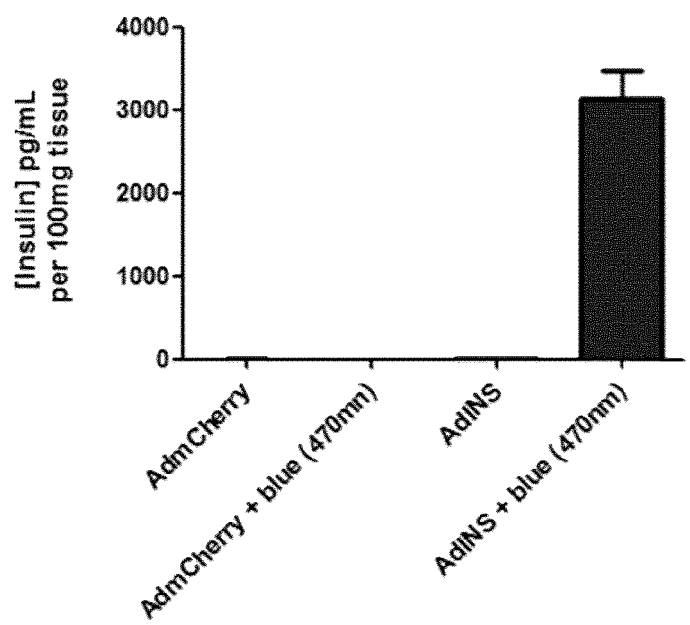
FIG. 6A shows that rat primary subcutaneous adipocytes transduced with the Ad-INS-ChIEF construct secrete insulin when stimulated with blue light.

An adenoviral delivery vector was then constructed. The adenovirus, referred to as Ad-INS-ChIEF, encodes a leptin leader peptide followed by a modified proinsulin sequence in which the PC1/3 and PC2 cleavage sites of the native proinsulin have been replaced by sites optimized for cleavage by furin, a protease which is expressed in adipocytes. This bioengineering design strategy has been chosen to facilitate processing of the proinsulin peptide in adipocytes as this cell type does not express the PC1/3 and PC2 proteases that normally cleave proinsulin in pancreatic beta-cells. Furthermore, the addition of the leptin leader sequence upstream of the first furin cleavage is expected to the proinsulin gene down the same processing, packaging and secretory pathway as leptin, a major peptide secreted by adipocytes. The viral DNA is bicistronic, encoding both the modified preproinsulin (preproINS$_{fur}$) and the ChR mutant ChIEF fused to the fluorescent protein reporter mCherry (FIGS. 1A to 1E). FIG. 4C shows data where the expression of mCherry can be clearly seen in 3T3-L1 transduced with the Ad-INS-ChIEF vector. These results indicate that the ChIEF-mCherry fusion protein is correctly folded and expressed in an adipocyte cell line.

In the next series of experiments, it was tested whether human insulin is expressed and secreted in a light-sensitive manner using the construct. Differentiated and cultured 3T3-L1 adipocyte cells or primary rat adipocytes were infected with either the viral vector Ad-INS-ChIEF or Ad-mCherry (as control) and cultured in the dark. After 48-72 hours, cells were kept in the dark or only exposed to red light (>600 nm) for practical purposes, as red light does not activate ChIEF but allows to work with the cells. Immediately after a media change, cells were exposed to either red light (as control) or pulsed blue light (470 nm) for various time durations. The supernatant was collected and analyzed for human insulin using a sensitive electrochemiluminescent assay (Meso Scale Discovery). Details of procedure are provided in Example 1 above. The results shown in FIGS. 5A, 5B, 6A and 6B show that insulin release is only induced when adipocytes infected with the Ad-INS-ChIEF vector were exposed to pulsed blue light. No insulin secretion was observed in either 3T3-L1 or primary rat adipocytes infected with the control AdmCherry virus. It is also worth noting that we a observed a weak insulin signal in Ad-INS-ChIEF infected cells in the absence of blue light exposure, suggesting that there may be a small "basal" amount of insulin released in those cells. This may be considered an advantage as this basal secretion may help control blood glucose levels in fasting conditions as observed previously[8].

Figure 8A:
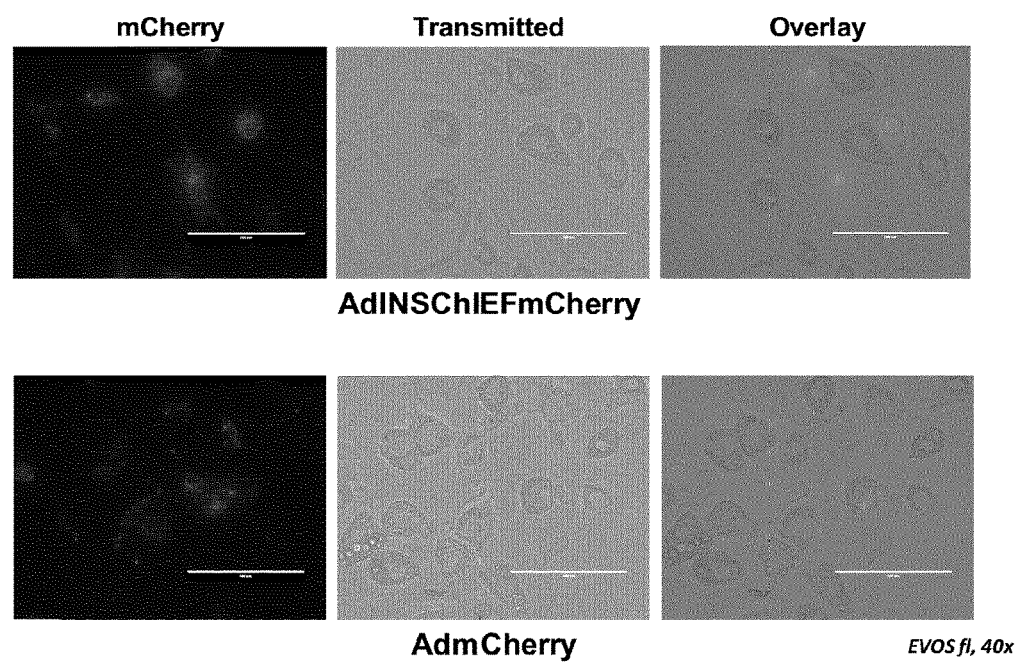
FIG. 8A shows representative images of transduction of primary rat adipocytes (inguinal white adipose tissue (WAT)) with 100 MOI of AdINSChIEFmCherry (upper panels) or control AdmCherry (lower panels).
Figure 8B:
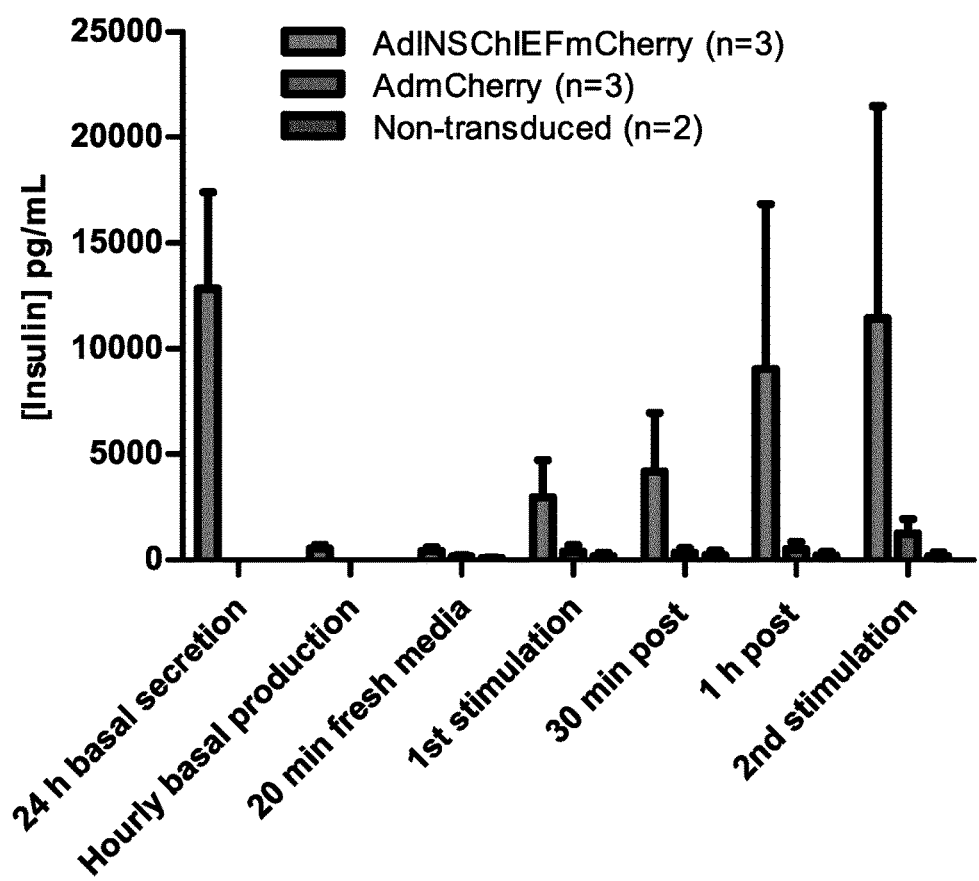
FIG. 8B shows insulin secretion following stimulation with pulsed blue (470 nm) light from primary rat adipocytes (inguinal WAT) non-transduced (right bars), transduced with control AdmCherry (middle bars) or with transduced with AdINSChIEFmCherry (left bars). Stimulation protocol: 20 s light on, 40 s off for 10 min total (1000 mA, 1 Hz).

FIG. 8A shows that primary rat adipocytes (from inguinal WAT) are transduced with AdINSChIEFmCherry (100 MOI). As shown in FIG. 8B, such AdINSChIEFmCherry-transduced primary rat adipocytes are able to secrete insulin following pulsed blue light (470 nm) stimulation in vitro. These results show that the adenoviral construct may be used to obtain engineered primary adipocytes capable of secreting insulin upon stimulation.

Figure 9A:
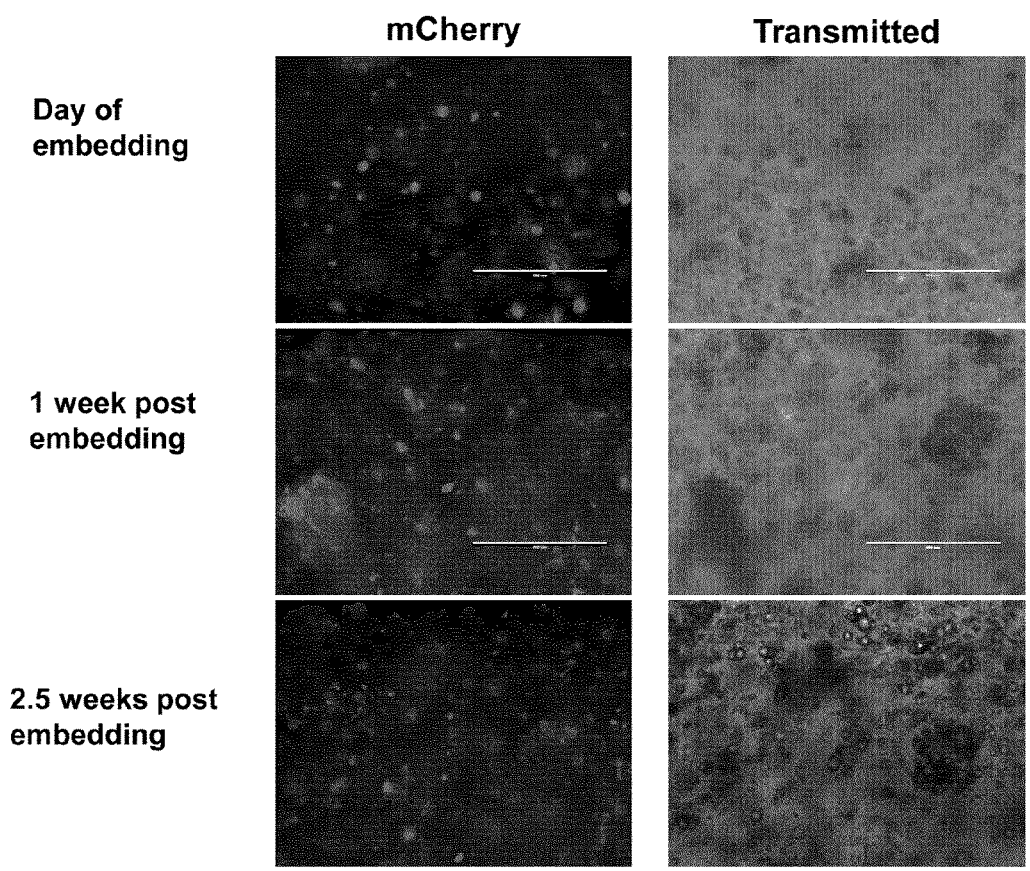
FIG. 9A shows representative images of Matrigel®-Embedded 3T3 L1 mature adipocytes transduced with Adm-Cherry at the day of embedding (upper panels), 1 week post-embedding (middle panels) and 2.5 weeks post-embedding (lower panels).
Figure 9B:
FIG. 9B shows a representative live in vivo image of AdINSChIEFmCherry-transduced, Matrigel®-Embedded, 3T3 L1 mature adipocytes. Lighter areas represent the locations of 3 Matrigel® grafts under the skin of a live mouse as determined by mCherry fluorescence that is expressed in the engineered adipocytes. Mouse strain used was Rag1$^{-/-}$ (C57BL/6). Image was taken one week after surgery.
Figure 10:
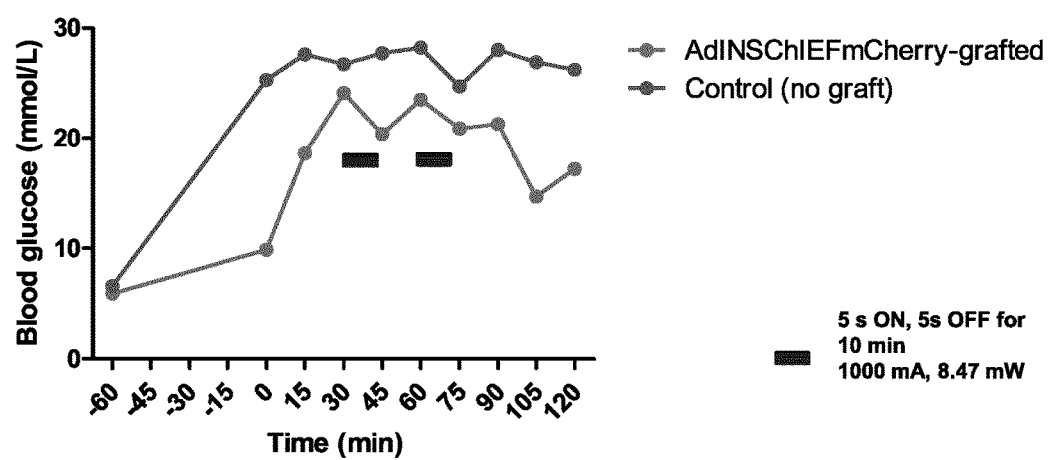
FIG. 10 shows the effects of blue light exposure on blood glucose levels in diazoxide-treated Rag1$^{-/-}$ mice grafted with AdINSChIEFmCherry-transduced, Matrigel®-embedded, 3T3 L1 mature adipocytes. Diazoxide was injected intraperitoneally (IP) 60 min prior to the start of the experiment as this drug inhibits endogenous insulin secretion from the mouse pancreas, causing a rise in blood glucose and allowing the assessment of the effects of insulin secreted from the graft. Results obtained in two mice are represented.

FIGS. 9A and 9B show that transduced 3T3 L1 mature adipocytes may be embedded in a Matrigel® Matrix and grafted in mice. It was next assessed whether AdINSChIEF-mCherry-transduced, Matrigel®-embedded 3T3 L1 mature adipocytes may be used to induce insulin secretion, and in turn to reduce blood glucose, in vivo. Diazoxide, a drug that inhibits endogenous insulin secretion from the pancreas, was administered to Rag1$^{-/-}$ C57BL/6 mice prior to the start of the experiment to induce a rise in blood glucose. As shown in FIG. 10, upon blue light stimulation, blood glucose was reduced in mice that received the Matrigel® grafts containing 9×10$^6$ engineered 3T3-L1 adipocytes (lower line), relative to the mice that did not receive a graft (upper line), thus providing evidence that the engineered adipocytes are able to secrete insulin upon stimulation in vivo, which in turns reduces blood glucose levels.

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

REFERENCES

1. Assady S, et al. (2001) Insulin production by human embryonic stem cells. Diabetes 50(8):1691-1697
2. Zulewski H, et al. (2001) Multipotential nestin-positive stem cells isolated from adult pancreatic islets differentiate ex vivo into pancreatic endocrine, exocrine, and hepatic phenotypes. Diabetes 50(3):521-533
3. Tang D-Q, et al. (2004) In vivo and in vitro characterization of insulin-producing cells obtained from murine bone marrow. Diabetes 53(7):1721-1732
4. Yang L, et al. (2002) In vitro trans-differentiation of adult hepatic stem cells into pancreatic endocrine hormone-producing cells. Proc Natl Acad Sci USA 99(12):8078-8083
5. Kojima H, et al. (2004) Extrapancreatic insulin-producing cells in multiple organs in diabetes. Proc Natl Acad Sci USA 101(8):2458-2463
6. Roy S S, et al. (2003) A new cell secreting insulin Endocrinology 144(4):1585-1593
7. Fujimoto K, et al. (2005) Enhanced insulin secretion from engineered 3T3-L1 preadipocytes by induction of cellular differentiation) Mol Cell Biochem 268(1-2):1-8
8. Ito M, et al. (2005) Implantation of primary cultured adipocytes that secrete insulin modifies blood glucose levels in diabetic mice. Diabetologia 48(8):1614-1620
9. Cammisotto P G & Bukowiecki L J (2004) Role of calcium in the secretion of leptin from white adipocytes. Am J Physiol Regul Integr Comp Physiol 287(6):R1380-1386
10. Oguri A, et al. (2010) Involvement of CaV3.1 T-type calcium channels in cell proliferation in mouse preadipocytes. Am J Physiol Cell Physiol 298(6):C1414-1423
11. Zhang X-H, et al, (2012) Functional ion channels and cell proliferation in 3T3-L1 preadipocytes. J Cell Physiol 227(5):1972-1979.
12. Lin J Y, Lin M Z, Steinbach P, Tsien R Y. Characterization of engineered channelrhodopsin variants with improved properties and kinetics. Biophys J. 2009 96(5): 1803-14.
13. Berndt A, Yizhar O, Gunaydin L A, Hegemann P, Deisseroth K. Bi-stable neural state switches. Nat Neurosci. 2009 12(2):229-34.
14. Klapoetke et al. Independent optical excitation of distinct neural populations. Nature Methods. 2014 March; 11(3):338-46.

What is claimed is:

1. An engineered adipocyte comprising:
   a first nucleic acid encoding a channelrhodopsin (ChR) polypeptide; and
   a second nucleic acid encoding a secretory polypeptide precursor comprising a bioactive polypeptide and a signal peptide suitable for secretion of said bioactive polypeptide by said engineered adipocyte, wherein said secretory polypeptide precursor is not naturally produced by a native adipocyte.

2. The engineered adipocyte of claim 1, wherein said secretory polypeptide precursor is a prohormone or preprohormone.

3. The engineered adipocyte of claim 2, wherein said preprohormone is preproinsulin and said bioactive polypeptide is insulin, wherein said preproinsulin comprises a recognition sequence for one or more proteases expressed by said engineered adipocyte, and wherein said one or more proteases is furin, tryptase, elastase or cathepsin K.

4. The engineered adipocyte of claim 3, wherein said one or more proteases is furin.

5. The engineered adipocyte of claim 4, wherein said recognition sequence comprises the amino acid sequence RXKR (SEQ ID NO:1), wherein X is any amino acid.

6. The engineered adipocyte of claim 1, wherein said signal peptide comprises a signal peptide from an adipokine.

7. The engineered adipocyte of claim 6, wherein said adipokine is human leptin.

8. The engineered adipocyte of claim 7, wherein said signal peptide comprises the amino acid sequence MHWGTLCGFLWLWPYLFYQA (SEQ ID NO:2).

9. The engineered adipocyte of claim 1, wherein said ChR polypeptide comprises the amino acid sequence of SEQ ID NO:10.

10. The engineered adipocyte of claim 1, wherein said first nucleic acid and/or second nucleic acid is/are operably linked to a viral promoter.

11. The engineered adipocyte of claim 1, wherein said first nucleic acid and/or second nucleic acid is/are operably linked to a promoter from a gene naturally expressed by native adipocytes.

12. The engineered adipocyte of claim 1, wherein said first nucleic acid and/or second nucleic acid is/are present in one or more vectors.

13. The engineered adipocyte of claim 12, wherein said vector is a viral vector.

14. The engineered adipocyte of claim 12, wherein said first nucleic acid and second nucleic acid are present in the same vector.

15. A vector comprising the first nucleic acid and second nucleic acid defined in claim 1.

* * * * *